United States Patent [19]

Hioki et al.

[11] Patent Number: 5,563,111

[45] Date of Patent: Oct. 8, 1996

[54] AGRICULTURAL CHEMICAL COMPOSITION COMPRISING AMINE SURFACTANTS WITH AT LEAST ONE ESTER OR AMIDE LINKAGE

[75] Inventors: Yuichi Hioki; Keiko Hasebe; Tadayuki Suzuki; Osamu Tachizawa; Takeshi Tomifuji; Tohru Katoh; Kohshiro Sotoya; Keiichiro Tomioka; Uichiro Nishimoto; Yoshifumi Nishimoto; Yasuki Ohtawa, all of Wakayama, Japan

[73] Assignee: Kao Corporation, Tokyo, Japan

[21] Appl. No.: 274,718

[22] Filed: Jul. 18, 1994

[30] Foreign Application Priority Data

Aug. 3, 1993 [JP] Japan ................... 5-192426
Dec. 15, 1993 [JP] Japan ................... 5-315309
Dec. 17, 1993 [JP] Japan ................... 5-318496

[51] Int. Cl.⁶ ............................ A01N 25/30
[52] U.S. Cl. ............. 504/116; 71/DIG. 1; 514/946; 514/975; 514/785; 514/788
[58] Field of Search ............. 504/116; 71/DIG. 1; 514/946, 975, 785, 788

[56] References Cited

U.S. PATENT DOCUMENTS

| 4,228,042 | 10/1980 | Letton | 252/528 |
|---|---|---|---|
| 4,883,917 | 11/1989 | Smith et al. | 564/292 |
| 4,888,049 | 12/1989 | Iwasaki et al. | 71/94 |
| 5,164,179 | 11/1992 | Hioki et al. | 424/78.08 |
| 5,430,005 | 7/1995 | Kassebaum et al. | 504/206 |

FOREIGN PATENT DOCUMENTS

| 0274369 | 7/1988 | European Pat. Off. . |
| 0509346 | 10/1992 | European Pat. Off. . |
| 3636994 | 5/1987 | Germany . |
| WO91/16024 | 10/1991 | WIPO . |

OTHER PUBLICATIONS

Chemical Patents Index, Documentation Abstracts Journal, Week 9032, Derwent Publications Ltd., London, GB; AN 90–242927/32 of JP–A–02 169 554 (Fajisawa Pharm) 29 Jun. 1990.

Central Patents Index, Basic Abstracts Journal, Week 8141, Derwent Publications Ltd., London, GB; AN 75021 D of JP–B–81 039 168 (Ajinomoto) 11 Sep. 1981.

*Primary Examiner*—S. Mark Clardy
*Attorney, Agent, or Firm*—Birch, Stewart, Kolasch & Birch, LLP

[57] ABSTRACT

A method for enhancing the effectiveness of an agricultural chemical which comprises incorporating a specific enhancer into a diluted solution of the agricultural chemical.

The specific enhancer is a quaternary ammonium salt or a amine.

37 Claims, No Drawings

AGRICULTURAL CHEMICAL COMPOSITION COMPRISING AMINE SURFACTANTS WITH AT LEAST ONE ESTER OR AMIDE LINKAGE

BACKGROUND OF THE INVENTION

1. Field of the Invention

The present invention relates to a method for enhancing the effectiveness of an agricultural chemical, a novel agricultural chemical composition containing a specific enhancer and a use of an enhancer for the preparation of the agricultural chemical composition.

2. Description of the Related Art

Agricultural chemicals including insecticides, fungicides (or bactericides), herbicides, miticides (or acaricides) and plant growth regulators have been used in the forms of, for example, emulsions, wettable powders, granules, powders and flowables. In the properties of these agricultural chemical preparations, various attempts have been made to achieve the maximum effectiveness of the agricultural chemicals. However, it has been difficult to enhance the effectiveness of agricultural chemicals through adjustments in formulations. It is further difficult to develop novel agricultural chemicals. Therefore, further enhancement of existing agricultural chemicals would highly contribute to the industry.

As substances capable of enhancing agricultural chemicals, surfactants comprising various nitrogen-containing compounds such as quaternary ammonium salts, betaines and amine oxides have been known (see European Patent Publication-A No. 274369, published on Jul. 13, 1988). It is known that quaternized or further polyoxyethylenated long-chain amines, among the above-mentioned compounds, are effective for this purpose. However, the enhancement effect of the above described compounds capable of enhancing agricultural chemicals is not always satisfactory.

DISCLOSURE OF THE INVENTION

Summary of the Invention

From the viewpoint that the effectiveness of the agricultural chemicals can be enhanced by the combined use of agricultural chemicals with quaternary ammonium salts or amines, the present inventors have conducted extensive studies. As a result, they have found that specific quaternary ammonium salts and amines are particularly effective in enhancing the effectiveness of various agricultural chemicals, thus completing the present invention.

Thus, the present invention provides an agricultural chemical composition comprising an agricultural chemical and an effective amount for enhancing the effectiveness of the agricultural chemical of an enhancer compound selected from the group consisting of compounds represented by the following formulae (A) to (F):

$$R^{2a}-\overset{R^{1a}}{\underset{R^{3a}}{\overset{|}{N^+}}}-CH_2\underset{O-(CH_2CHO)_n-\underset{R^{5a}}{\overset{|}{C}}-R^{6a}}{\overset{|}{CH}}CH_2-R^{4a} \cdot X^- \quad (A)$$

wherein $R^{1a}$ and $R^{2a}$ may be the same or different from each other and each represents an alkyl group having 1 to 4 carbon atoms, a group represented by the formula:

$$-(CH_2CHO)_{m1}-H$$
$$\underset{R^{7a}}{|}$$

(wherein each of $R^{7a}$s represents a hydrogen atom or a methyl group, and m1 is from 1 to 30) or a group represented by the formula:

$$-(CH_2CHO)_{m2}-\underset{O}{\overset{||}{C}}-R^{13a}$$
$$\underset{R^{14a}}{|}$$

(wherein $R^{13a}$ represents a linear or branched alkyl or alkenyl group having 5 to 36 carbon atoms which may be substituted by a hydroxyl group, each of $R^{14a}$s represents a hydrogen atom or a methyl group, and m2 is from 1 to 30);

$R^{3a}$ represents a hydrogen atom, a benzyl group or an alkyl group having 1 to 4 carbon atoms, preferably a hydrogen atom or an alkyl group having 1 to 4 carbon atoms;

$R^{4a}$ represents a group represented by the formula:

$$-O-(CH_2CHO)_{q1}-\underset{O}{\overset{||}{C}}-R^{9a}$$
$$\underset{R^{8a}}{|}$$

(wherein each of $R^{8a}$s represents a hydrogen atom or a methyl group, $R^{9a}$ represents a linear or branched alkyl or alkenyl group having 5 to 36 carbon atoms which may be substituted with a hydroxyl group, and q1 is from 0 to 30), a group represented by the formula: $-NHCOR^{10a}$ (wherein $R^{10a}$ represents a linear or branched alkyl or alkenyl group having 5 to 36 carbon atoms which may be substituted with a hydroxyl group) or a group represented by the formula:

$$-O-(CHCH_2O)_{q2}-R^{12a}$$
$$\underset{R^{11a}}{|}$$

(wherein each of $R^{11a}$s represents a hydrogen atom or a methyl group, $R^{12a}$ represents a linear or branched alkyl or alkenyl group having 5 to 36 carbon atoms which may be substituted with a hydroxyl group, and q2 is from 0 to 30);

each of $R^{5a}$s represents a hydrogen atom or a methyl group;

$R^{6a}$ represents a linear or branched alkyl or alkenyl group having 5 to 35 carbon atoms which may be substituted with a hydroxyl group;

n is from 0 to 30; and $X^-$ represents a counter ion, $$\underset{R^{2b}}{\overset{R^{1b}}{\diagdown}} N-CH_2\underset{\underset{O}{\overset{||}{OCC_tH_{2t}(OCHCH_2)_vOR^{4b}}}}{\overset{|}{CH}CH_2O\overset{O}{\overset{||}{C}}C_uH_{2u}(OCHCH_2)_wOR^{3b}} \quad (B)$$

wherein $R^{1b}$ and $R^{2b}$ may be the same or different from each other and each represents an alkyl group having 1 to 4 carbon atoms which may be substituted with a hydroxyl group, preferably an alkyl group having 1 to 4 carbon atoms;

$R^{3b}$ and $R^{4b}$ may be the same or different from each other and each represents a linear or branched alkyl or alkenyl group having 4 to 36 carbon atoms which may be substituted with a hydroxyl group;

each of $R^{5b}$s and $R^{6b}$s represents a hydrogen atom or a methyl group;

t and u may be the same or different from each other and each represents a positive number of from 1 to 5; and v and w may be the same or different from each other and each represents a number of from 0 to 30,

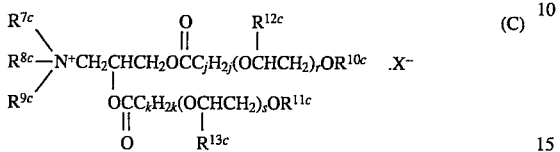 (C)

wherein $N^{7c}$ and $R^{8c}$ may be the same or different from each other and each represents an alkyl group having 1 to 4 carbon atoms;

$R^{9c}$ represents a hydrogen atom, a benzol group or an alkyl group having 1 to 4 carbon atoms, preferably a hydrogen atom or an alkyl group having 1 to 4 carbon atoms;

$R^{10c}$ and $R^{11c}$ may be the same or different from each other and each represents a linear or branched alkyl or alkenyl group having 4 to 36 carbon atoms which may be substituted with a hydroxyl group;

each of $R^{12c}$s and $R^{13c}$s represents a hydrogen atom or a methyl group;

j and k may be the same or different from each other and each represents a positive number of from 1 to 5;

r and s may be the same or different from each other and each represents a number of from 0 to 30; and $X^-$ represents a counter ion,

 (D)

wherein $R^{1d}$ represents an alkyl group having 1 to 4 carbon atoms which may be substituted with a hydroxyl group;

$R^{2d}$ represents a linear or branched alkyl or alkenyl group having 1 to 36 carbon atoms, preferably 5 to 36 carbon atoms, which may be substituted with a hydroxyl group, a group represented by the formula: $-C_aH_{2a}-(G^1)-R^{4d}$ (wherein $R^{4d}$ represents a linear or branched alkyl or alkenyl group having 5 to 36 carbon atoms which may be substituted with a hydroxyl group, $G^1$ represents a group represented by the formula: $-OCO-$ or a group represented by the formula: $-NHCO-$, and a represents a positive number of 2 to 6), a group represented by the formula:

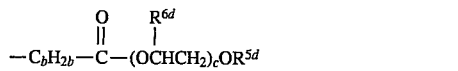

(wherein $R^{5d}$ represents a linear or branched alkyl or alkenyl group having 6 to 36 carbon atoms which may be substituted with a hydroxyl group, each of $R^{6d}$s represents a hydrogen atom or a methyl group, b represents a positive number of 1 to 5, and c represents a number of 0 to 30) or a group represented by the formula:

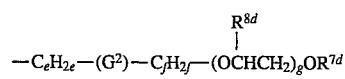

(wherein $R^{7d}$ represents a linear or branched alkyl or alkenyl group having 4 to 36 carbon atoms which may be substituted with a hydroxyl group, each of $R^{8d}$s represents a hydrogen atom or a methyl group, $G^2$ represents a group represented by the formula: $-OCO-$ or a group represented by the formula: $-NHCO-$, e represents a positive number of 2 to 6, f represents a positive number of 1 to 5 and g represents a number of 0 to 30); and $R^{3d}$ represents a group represented by the formula:

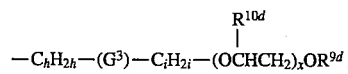

(wherein $R^{9d}$ represents a linear or branched alkyl or alkenyl group having 4 to 36 carbon atoms which may be substituted with a hydroxyl group, each of $R^{10d}$s represents a hydrogen atom or a methyl group, $G^3$ represents a group represented by the formula: $-OCO-$ or a group represented by the formula: $-NHCO-$, h represents a positive number of 2 to 6, i represents a positive number of 1 to 5, and x represents a number of 0 to 30) or a group represented by the formula:

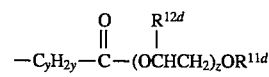

(wherein $R^{11d}$ represents a linear or branched alkyl or alkenyl group having 6 to 36 carbon atoms which may be substituted with a hydroxyl group, each of $R^{12d}$s represents a hydrogen atom or a methyl group, y represents a positive number of 1 to 5, and z represents a number of 0 to 30),

 (E)

wherein $R^e$ represents a hydrogen atom, a benzyl group or an alkyl group having 1 to 4 carbon atoms which may be substituted with a hydroxyl group, preferably a hydrogen atom or an alkyl group having 1 to 4 carbon atoms which may be substituted with a hydroxyl group;

$R^{1e}$ represents an alkyl group having 1 to 4 carbon atoms which may be substituted with a hydroxyl group;

$R^{2e}$ represents a linear or branched alkyl or alkenyl group having 1 to 36 carbon atoms, preferably 5 to 36 carbon atoms, which may be substituted with a hydroxyl group, a group represented by the formula: $-C_aH_{2a}-(G^1)-R^{4e}$ (wherein $R^{4e}$ represents a linear or branched alkyl or alkenyl group having 5 to 36 carbon atoms which may be substituted with a hydroxyl group, $G^1$ represents a group represented by the formula: $-OCO-$ or a group represented by the formula: $-NHCO-$, and a represents a positive number of 2 to 6), a group represented by the formula:

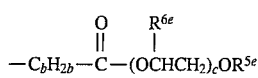

(wherein $R^{5e}$ represents a linear or branched alkyl or alkenyl group having 6 to 36 carbon atoms which may be substituted with a hydroxyl group, each of $R^{6e}$s represents a hydrogen atom or a methyl group, b represents a positive number of 1 to 5, and c represents a number of 0 to 30) or a group represented by the formula:

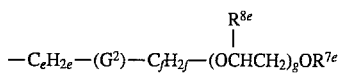

(wherein $R^{7e}$ represents a linear or branched alkyl or alkenyl group having 4 to 36 carbon atoms which may be substituted with a hydroxyl group, each of $R^{8e}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of 0 to 30);

$R^{3e}$ represents a group represented by the formula:

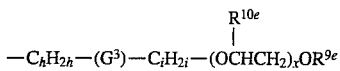

(wherein $R^{9e}$ represents a linear or branched alkyl or alkenyl group having 4 to 36 carbon atoms which may be substituted with a hydroxyl group, each of R10es represents a hydrogen atom or a methyl group, $G^3$ represents a group represented by the formula: —OCO— or a group represented by the formula: —NHCO—, h represents a positive number of 2 to 6, i represents a positive number of 1 to 5, and x represents a number of 0 to 30) or a group represented by the formula:

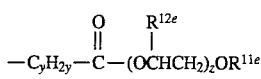

(wherein $R^{11e}$ represents a linear or branched alkyl or alkenyl group having 6 to 36 carbon atoms which may be substituted with a hydroxyl group, each of $R^{12e}$s represents a hydrogen atom or a methyl group, y represents a positive number of 1 to 5, and z represents a number of 0 to 30); and $X^-$ represents a counter ion, and

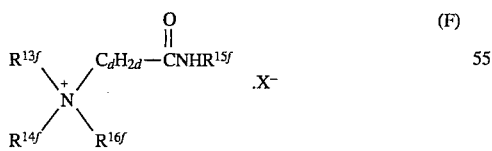

wherein $R^{13f}$ represents a hydrogen atom, a benzyl group or an alkyl group having 1 to 4 carbon atoms which may be substituted with a hydroxyl group, preferably a hydrogen atom or an alkyl group having 1 to 4 carbon atoms which may be substituted with a hydroxyl group;

$R^{14f}$ represents an alkyl group having 1 to 4 carbon atoms which may be substituted with a hydroxyl group;

$R^{15f}$ represents a linear or branched alkyl or alkenyl group having 6 to 36 carbon atoms which may be substituted with a hydroxyl group; $R^{16f}$ represents a linear or branched alkyl or alkenyl group having 5 to 36 carbon atoms which may be substituted with a hydroxyl group;

d is a positive number of 1 to 5; and $X^-$ is a counter ion.

Examples of the counter ion include a halide ion such as $Cl^-$, $Br^-$ and $I^-$, an alkylsulfate anion ($RSO_4^-$), an alkylbenzenesulfonic acid anion (R-benzene-$SO_3^-$), an alkylnaphthalenesulfonic acid anion (R-naphthalene-$SO_3^-$), a fatty acid anion ($RCOO^-$), an alkylphosphate anion ($ROPO_3H^-$) (wherein R represents an alkyl group), an anionic oligomer and an anionic polymer.

The enhancer compound according to the present invention include those represented by the following formulae (I-A) to (I-F):

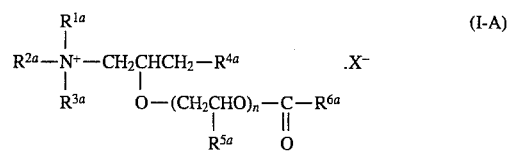

wherein $R^{1a}$, $R^{2a}$: either the same or different, an alkyl group having 1 to 4 carbon atoms,

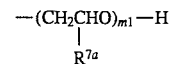

($R^{7a}$: hydrogen or a methyl group(s), or a mixture of hydrogen with a methyl group(s), m1: 1~30) or

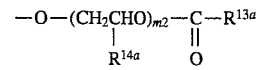

($R^{14a}$: hydrogen or a methyl group(s), or a mixture of hydrogen with a methyl group(s), m2: 1~30);

$R^{3a}$: hydrogen or an alkyl group having 1 to 4 carbon atoms;

$R^{4a}$:

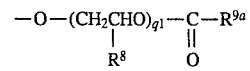

($R^{8a}$: hydrogen or a methyl group(s), or a mixture of hydrogen with a methyl group(s), q1: 0~30 ), —$NHCOR^{10a}$ or

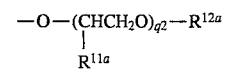

($R^{11a}$: hydrogen or a methyl group(s), or a mixture of hydrogen with a methyl group(s), q2: 0~30), $R^{9a}$, $R^{10a}$, $R^{12a}$, $R^{13a}$: a linear or branched alkyl or alkenyl group having 5 to 36 carbon atoms which may be substituted with a hydroxyl group;

$R^{5a}$: hydrogen or a methyl group(s), or a mixture of hydrogen with a methyl group(s);

n: 0~30;

$R^{6a}$: a linear or branched alkyl or alkenyl group having 5 to 35 carbon atoms which may be substituted with a hydroxyl group; and $X^-$: a counter ion, $$\begin{array}{c} R^{1b} \\ \diagdown \\ \phantom{R^{2b}}NCH_2CHCH_2OCC_uH_{2u}(OCHCH_2)_wOR^{3b} \\ \diagup \phantom{NCH_2CHCH_2O} | \phantom{{}_uH_{2u}(OCH)} | \\ R^{2b} \phantom{NCH_2} OCC_tH_{2t}(OCHCH_2)_vOR^{4b} \\ \phantom{R^{2b}NCH_2} \| \phantom{C_tH_{2t}(OCH)} | \\ \phantom{R^{2b}NCH_2} O \phantom{C_tH_{2t}(OCHCH_2)_v} R^{6b} \end{array} \quad \text{(I-B)}$$

wherein $R^{1b}$, $R^{2b}$: either the same or different, an alkyl group having 1 to 4 carbon atoms;

$R^{3b}$, $R^{4b}$: a linear or branched alkyl or alkenyl group having 4 to 36 carbon atoms which may be substituted with a hydroxyl group;

$R^{5b}$, $R^{6b}$: hydrogen or a methyl group(s), or a mixture of hydrogen with a methyl group(s);

t, u: either the same or different, a positive number of 1~5; and v, w: either the same or different, a positive number of 0~30 on the average, $$\begin{array}{c} R^{7c} \\ \diagdown + \phantom{NCH_2CHCH_2OC} O \phantom{OCH} R^{12c} \\ \phantom{R^{8c}}\diagdown \phantom{CHCH_2OCC_jH_{2j}(O)} \| \phantom{OCH_2)_r} | \\ R^{8c}-NCH_2CHCH_2OCC_jH_{2j}(OCHCH_2)_rOR^{10c}.X^- \\ \diagup \phantom{NCH_2CHCH_2O} | \\ R^{9c} \phantom{NCH} OCC_kH_{2k}(OCHCH_2)_sOR^{11c} \\ \phantom{R^{9c}NCH} \| \phantom{C_kH_{2k}(OCH)} | \\ \phantom{R^{9c}NCH} O \phantom{C_kH_{2k}(OCHCH_2)_s} R^{13c} \end{array} \quad \text{(I-C)}$$

wherein $R^{7c}$, $R^{8c}$: either the same or different, an alkyl group having 1 to 4 carbon atoms;

$R^{9c}$: hydrogen or an alkyl group having 1 to 4 carbon atoms;

$R^{10c}$, $R^{11c}$: a linear or branched alkyl or alkenyl group having 4 to 36 carbon atoms which may be substituted with a hydroxyl group;

$R^{12c}$, $R^{13c}$: hydrogen or a methyl group(s), or a mixture of hydrogen with a methyl group(s);

j, k: either the same or different, a positive number of 1~5;

r, s: either the same or different, a positive number of 0~30 on the average; and $X^-$: a counter ion, $$\begin{array}{c} \phantom{R^{1d}-N}R^{2d} \\ \phantom{R^{1d}-N}\diagup \\ R^{1d}-N \\ \phantom{R^{1d}-N}\diagdown \\ \phantom{R^{1d}-N}R^{3d} \end{array} \quad \text{(I-D)}$$

wherein $R^{1d}$: an alkyl group having 1 to 4 carbon atoms which may be substituted with a hydroxyl group;

$R^{2d}$: a linear or branched alkyl or alkenyl group having 5 to 36 carbon atoms which may be substituted with a hydroxyl group, $$-C_aH_{2a}-(G^1)-R^{4d}(G^1: \underset{\|}{-O}\underset{O}{C}- \text{ or } \underset{\|}{-N}\underset{O}{H}C-),$$

$$-C_bH_{2b}-\underset{\|}{C}-(OCHCH_2)_cOR^{5d} \text{ or}$$

$$-C_eH_{2e}-(G^2)-C_fH_{2f}-(OCHCH_2)_gOR^{7d}(G^2: \underset{\|}{-O}\underset{O}{C}- \text{ or}$$

$$-\underset{\|}{N}\underset{O}{H}C-); R^{3d}: -C_hH_{2h}-(G^3)-C_iH_{2i}-(OCHCH_2)_xOR^{9d}$$

$$(G^3: \underset{\|}{-O}\underset{O}{C}- \text{ or } \underset{\|}{-N}\underset{O}{H}C-) \text{ or}$$

$$-C_yH_{2y}-\underset{\|}{C}-(OCHCH_2)_zOR^{11d};$$

$R^{4d}$: a linear or branched alkyl or alkenyl group having 5 to 36 carbon atoms which may be substituted with a hydroxyl group;

$R^{5d}$, $R^{11d}$: either the same or different, a linear or branched alkyl or alkenyl group having 6 to 36 carbon atoms which may be substituted with a hydroxyl group;

$R^{7d}$, $R^{9d}$: either the same or different, a linear or branched alkyl or alkenyl group having 4 to 36 carbon atoms which may be substituted with a hydroxyl group;

$R^{6d}$, $R^{8d}$, $R^{10d}$, $R^{12d}$: either the same or different, hydrogen or a methyl group(s), or a mixture of hydrogen with a methyl group(s);

c, g, x, z: either the same or different, a positive number of 0~30 on the average;

a, e, h: the same or different, a positive number of 2~6; and b, f, i, y: either the same or different, a positive number of 1~5, $$\begin{array}{c} \phantom{R^{1e}}R^e \phantom{XXX} R^{2e} \\ \phantom{R^{1e}}\diagdown + \diagup \\ \phantom{R^{1e}}N \phantom{XX} .X^- \\ \phantom{R^{1e}}\diagup \phantom{XX} \diagdown \\ R^{1e} \phantom{XXXXX} R^{3e} \end{array} \quad \text{(I-E)}$$

wherein $R^e$: hydrogen or an alkyl group having 1 to 4 carbon atoms which may be substituted with a hydroxyl group;

$R^{1e}$: an alkyl group having 1 to 4 carbon atoms which may be substituted with a hydroxyl group;

$R^{2e}$: a linear or branched alkyl or alkenyl group having 5 to 36 carbon atoms which may be substituted with a hydroxyl group, $$-C_aH_{2a}-(G^1)-R^{4e}(G^1: \underset{\|}{-O}\underset{O}{C}- \text{ or } \underset{\|}{-N}\underset{O}{H}C-),$$

$$-C_bH_{2b}-\underset{\|}{C}-(OCHCH_2)_cOR^{5e} \text{ or}$$

$$-C_eH_{2e}-(G^2)-C_fH_{2f}-(OCHCH_2)_gOR^{7e}(G^2: \underset{\|}{-O}\underset{O}{C}- \text{ or}$$

$$-\underset{\|}{N}\underset{O}{H}C-); R^{3e}: -C_hH_{2h}-(G^3)-C_iH_{2i}-(OCHCH_2)_xOR^{9e}$$

$$(G^3: \underset{\|}{-O}\underset{O}{C}- \text{ or } \underset{\|}{-N}\underset{O}{H}C-) \text{ or}$$

$$-C_yH_{2y}-\underset{\|}{C}-(OCHCH_2)_zOR^{11e};$$

$R^{4e}$: a linear or branched alkyl or alkenyl group having 5 to 36 carbon atoms which may be substituted with a hydroxyl group;

$R^{5e}$, $R^{11e}$: either the same or different, a linear or branched alkyl or alkenyl group having 6 to 36 carbon atoms which may be substituted with a hydroxyl group;

$R^{7e}$, $R^{9e}$: either the same or different, a linear or branched alkyl or alkenyl group having 4 to 36 carbon atoms which may be substituted with a hydroxyl group;

$R^{6e}$, $R^{8e}$, $R^{10e}$, $R^{12e}$: either the same or different, hydrogen or a methyl group(s), or a mixture of hydrogen with a methyl group(s);

c, g, x, z: either the same or different, a positive number of 0~30 on the average;

a, e, h: the same or different, a positive number of 2~6;

b, f, i, y: either the same or different, a positive number of 1~5; and $X^-$: a counter ion,

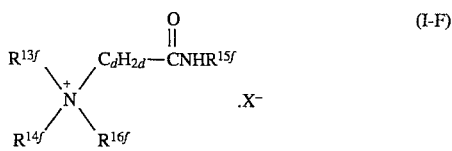

(I-F)

wherein $R^{13f}$: hydrogen or an alkyl group having 1 to 4 carbon atoms which may be substituted with a hydroxyl group;

$R^{14f}$: an alkyl group having 1 to 4 carbon atoms which may be substituted with a hydroxyl group;

$R^{15f}$: a linear or branched alkyl or alkenyl group having 6 to 36 carbon atoms which may be substituted with a hydroxyl group;

R16f: a linear or branched alkyl or alkenyl group having 5 to 36 carbon atoms which may be substituted with a hydroxyl group;

d: a positive number of 1~5; and $X^-$: a counter ion.

Further, the present invention provides a method for enhancing the effectiveness of an agricultural chemical which comprises applying an enhancer compound selected from the group consisting of compounds represented by the above formulae (A) to (F) with an agricultural chemical to a locus which would benefit from such treatment. In this method, the enhancer compound and the agricultural chemical are generally diluted with water or a liquid carrier.

Examples of the locus or the area to be treated include farm, plantation, fruit garden, orchard, flower garden, lawn, wood and forest. Examples of the locus include, further, plants, crops such as cereals, vegetables and fruits, trees, fruit trees, grasses, weeds, seeds, fungi, bacteria, insects, acarids and mites.

Furthermore, the present invention provides a use of an enhancer compound selected from the group consisting of compounds represented by the above formulae (A) to (F) for the preparation of an agricultural chemical composition, an enhancer (or an adjuvant) for agricultural chemicals comprising a compound selected from the group consisting of compounds represented by the above formulae (A) to (F); and a use of the enhancer for enhancing the effectiveness of an agricultural chemical.

In addition, the present invention provides an agricultural chemical kit which comprises a container containing the enhancer described above and a container containing an agricultural chemical composition; another agricultural chemical kit which comprises a container containing the enhancer described above and a surfactant other than the compounds represented by the above formulae (A) to (F) and a container containing an agricultural chemical composition; and another agricultural chemical kit which comprises a container containing the enhancer described above, a container containing a surfactant other than the compounds represented by the above formulae (A) to (F) and a container containing an agricultural chemical composition.

In this specification, the term "agricultural chemical" means one which is employed as an active or principle ingredient in common agricultural chemical compositions or preparations, and examples thereof include a fungicide (or a bactericide), an insecticide, a miticide (or an acaricide), a herbicide, a plant growth regulator and the like.

Further the scope and the applicability of the present invention will become apparent from the detailed description given hereinafter. However, it should be understood that the detailed description and specific examples which follow, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the present invention, compounds represented by the above formulae (A) to (F) are used as enhancers for agricultural chemicals.

When the compound of the formula (A) according to the present invention is a quaternary ammonium salt of diester type, it may be obtained by, for example, reacting 3-chloropropane-1,2-diol with dimethylamine to dehydrochlorinate, neutralizing and purifying the obtained product to thereby give dimethylaminopropane-1,2-diol, reacting this compound with a fatty acid to esterify and then quaternizing the ester thus obtained with, for example, an alkyl chloride.

An alkylene oxide adduct of an ammonium salt of diester type may be obtained by synthesizing dimethyl-aminopropane-1,2-diol by the above-mentioned method, adding, for example, ethylene oxide to this product with the use of KOH as a catalyst, esterifying the obtained adduct and then quaternizing the product or converting the product into an acidic salt thereof.

An acidic salt of ester amide type may be obtained by reacting 2-hydroxypropylenediamine with a fatty acid to thereby give a tatrahydropyridine derivative, hydrolyzing this derivative to thereby give an aminohydroxyamide, dimethylating the amide by the reductive methylation method, esterifying the resulting compound by reacting it with a fatty acid to thereby give a dimethylamine of ester amide type and then reacting this compound with an acidic substance such as hydrochloric acid.

It is needless to say that methods for the preparation of the compound of the formula (A) according to the present invention are not restricted to those cited above.

In the formula (A), it is preferable that $R^{6a}$, $R^{9a}$, $R^{10a}$, $R^{12a}$ and $R^{13a}$ have each 7 to 22 carbon atoms, $R^{1a}$ and $R^{2a}$ are each a methyl group, and $R^{3a}$ is a hydrogen atom, an alkyl group having 1 or 2 carbon atoms or a benzyl group, still more preferably a hydrogen atom or an alkyl group having 1 or 2 carbon atoms. In the case of compounds having alkylene oxide added thereto, the average addition mole numbers of the alkylene oxide (m1, m2, n, q1, q2) are each preferably from 1 to 20, and still more preferably from 1 to 15.

The formula (A) represents also a mixture of compounds which are different from one another the addition mole number of the alkylene oxide and/or the kind of the alkylene oxide to be added, in addition to a single compound. When the single compound or the compounds which are composed of the mixture has(have) two or more $R^{5a}$s (or $R^{7a}$s, $R^{8a}$s, $R^{11a}$s or $R^{14a}$s), the $R^{5a}$s (or $R^{7a}$s, $R^{8a}$s, $R^{11a}$s or $R^{14a}$s) may be the same or different from one another. In other words, the alkylene oxide to be added is ethylene oxide, propylene oxide or a mixture of ethylene oxide with propylene oxide.

The compound of the formula (B) according to the present invention may be obtained by reacting 3-chloropropane-1,2-diol with dimethylamine to dehydrochlorinate, neutralizing and purifying the obtained product to thereby give dimethylaminopropane- 1,2-diol and esterifying this compound by reacting it with polyoxyethylene ether carboxylic acid. It is needless to say that the method for preparing the compound of the formula (B) according to the present invention is not restricted thereto.

In the formula (B), it is preferable that $R^{1b}$ and $R^{2b}$ are each a methyl group, $R^{3b}$ and $R^{4b}$ are each an alkyl or alkenyl group having 4 to 22 carbon atoms, t and u are each from 1 to 3, and v and w, which represent each the average addition mole number of the alkylene oxide, are each from 0 to 20. Furthermore, in the above case, v and w are each still more preferably from 1 to 15, and the total number of v and w is preferably from 2 to 30.

The formula (B) represents also a mixture of compounds which are different from one another the addition mole number of the alkylene oxide and/or the kind of the alkylene oxide to be added, in addition to a single compound. When the single compound or the compounds which are composed of the mixture has(have) two or more $R^{5b}$s (or $R^{6b}$s), the $R^{5b}$s (or $R^{6b}$s) may be the same or different from one another. In other words, the alkylene oxide to be added is ethylene oxide, propylene oxide or a mixture of ethylene oxide with propylene oxide.

The compound of the formula (C) according to the present invention may be obtained by quaternizing the compound represented by the above formula (B) with, for example, an alkyl chloride. It is needless to say that the method for preparing the compound of the formula (C) according to the present invention is not restricted thereto.

In the above formula (C), it is preferable that $R^{7c}$ and $R^{8c}$ are each a methyl group, $R^{9c}$ is a methyl, ethyl or benzyl group, $R^{10c}$ and $R^{11c}$ are each an alkyl or alkenyl group having 4 to 22 carbon atoms, j and k are each from 1 to 3, and r and s, which represent each the average addition mole number of the alkylene oxide, are each from 0 to 20. Furthermore, in the above case, it is still more preferable that $R^{9c}$ is a methyl or ethyl group, r and s are each from 1 to 15, and the total number of r and s is from 2 to 30.

The formula (C) represents also a mixture of compounds which are different from one another the addition mole number of the alkylene oxide and/or the kind of the alkylene oxide to be added, in addition to a single compound. When the single compound or the compounds which are composed of the mixture has(have) two or more $R^{12c}$s(or $R^{13c}$s), the $R^{12c}$s(or $R^{13c}$s) may be the same or different from one another. In other words, the alkylene oxide to be added is ethylene oxide, propylene oxide or a mixture of ethylene oxide with propylene oxide.

Among the compounds of the formula (D) according to the present invention, an amine of a diester type can be obtained by, for example, reacting monochloroacetic acid with a polyoxyethylene alkyl ether to thereby effect esterification and then reacting the chloroester compound thus obtained with methylamine to dehydrochlorinate. An amine of a diester type wherein one of functional groups is in the reverse direction may be obtained by, for example, reacting 2-chloroethanol with polyoxyethylene ether carboxylic acid to thereby effect esterification, reacting the chloroester compound thus obtained with methylamine to dehydrochlorinate, and then reacting the amine ester compound thus obtained with, for example, a chloroester compound obtained from monochloroacetic acid and a polyoxyethylene alkyl ether to dehydrochlorinate. An amine of another diester type may be obtained by, for example, reacting diethanolmethylamine with polyoxyethylene ether carboxylic acid to thereby effect esterification. An amine of an ester amide type may be obtained by, for example, reacting N-hydroxyethyl-N-methylpropanediamine with polyoxyethylene ether carboxylic acid to thereby effect esterification and amidation. An amine of a diamide type may be obtained by, for example, reacting 3,3'-diamino-N-methyldipropylamine with polyoxyethylene ether carboxylic acid to thereby effect amidation. An amine of an alkyl ester type may be obtained by, for example, reacting chlorododecane with methylamine to thereby effect dehydrochlorination and then reacting the secondary amine compound thus obtained with a chloroester compound to thereby effect dehydrochlorination. An amine of an alkylamide type may be obtained by, for example, reacting N-ethylethylenediamine with polyoxyethylene ether carboxylic acid to thereby effect amidation and then reacting the aminoamide compound thus obtained with an alkyl chloride to thereby effect dehydrochlorination.

The compound of the formula (E) according to the present invention can be obtained by, for example, quaternizing a compound of the formula (D) with an alkyl chloride.

The compound of the Formula (F) according to the present invention can be obtained by, for example, reacting dimethyldodecylamine with a chloroester compound to thereby effect quaternization and then substituting a secondary amino group for the alcoholic hydroxyl group in the ester quaternary ammonium salt compound thus obtained by reacting said compound with, for example, dodecylamine to thereby effect amidation.

It is needless to say that methods for the preparation of the compounds of the Formulae (D), (E) and (F) according to the present invention are not restricted to those cited above.

Among the compounds of the formula (D) according to the present invention, preferable ones are those wherein $R^{1d}$ is a methyl, ethyl or hydroxyethyl group, $R^{2d}$ is an alkyl group having 1 to 22 carbon atoms provided that it represents an alkyl group, $R^{4d}$ is an alkyl group having 7 to 2 carbon atoms, $R^{5d}$ and $R^{11d}$ are each an alkyl group having 8 to 22 carbon atoms, $R^{7d}$ and $R^{9d}$ are each an alkyl group having 4 to 22 carbon atoms, c, g, x and z, which represent each the average addition mole number of the alkylene oxide, are each a number of 0 to 20, a, e and h are each a number of from 2 to 4, and b, f, i and y are each a number of from 1 to 3. Furthermore, in the above case, it is still more preferable that $R^{2d}$ is an alkyl group having 8 to 22 carbon atoms, and c, g, x and z are each a number of 1 to 15.

The formula (D) represents also a mixture of compounds which are different From one another the addition mole number of the alkylene oxide and/or the kind of the alkylene oxide to be added, in addition to a single compound. When the single compound or the compounds which are composed of the mixture has(have) two or more $R^{6d}$s(or $R^{5d}$s, $R^{10d}$s or $R^{12d}$s), the $R^{6d}$s (or $R^{8d}$s, $R^{10d}$s or $R^{12d}$s) may be the same or different from one another. In other words, the alkylene oxide to be added is ethylene oxide, propylene oxide or a mixture of ethylene oxide with propylene oxide.

Among the compounds of the formula (E) according to the present invention, preferable ones are those wherein $R^e$ is a hydrogen atom, an alkyl group having 1 to 2 carbon atoms or a benzyl group, $R^{1e}$ is a methyl, ethyl or hydroxyethyl group, $R^{2e}$ is an alkyl group having 1 to 22 carbon atoms provided that it represents an alkyl group. $R^{4e}$ is an alkyl group having 7 to 21 carbon atoms, $R^{5e}$ and $R^{11e}$ are each an alkyl group having 8 to 22 carbon atoms, $R^{7e}$ and $R^{9e}$ are each an alkyl group having 4 to 22 carbon atoms, c, g, x and z, which represent each the average addition mole number of the alkylene oxide, are each a number of 0 to 20, a, e and h are each a number of from 2 to 4, and b, f, i and y are each a number of from 1 to 3. Further, still more preferable ones are those wherein $R^e$ is a hydrogen atom or an alkyl group having 1 to 2 carbon atoms, $R^{1e}$ is a methyl, ethyl or hydroxyethyl group, $R^{2e}$ is an alkyl group having 8 to 22 carbon atoms provided that it represents an alkyl group, $R^{4e}$ is an alkyl group having 7 to 21 carbon atoms, $R^{5e}$ and $R^{11e}$ are each an alkyl group having 8 to 22 carbon atoms, $R^{7e}$ and $R^{9e}$ are each an alkyl group having 4 to 22 carbon atoms, c, g, x and z, which represent each the average addition mole number of the alkylene oxide, are each a number of 1 to 15, a, e and h are each a number of from 2 to 4, and b, f, i and y are each a number of from 1 to 3.

The formula (E) represents also a mixture of compounds which are different from one another in the addition mole number of the alkylene oxide and/or the kind of the alkylene oxide to be added, in addition to a single compound. When the single compound or the compounds which are composed of the mixture has(have) two or more $R^{6e}$s (or $R^{8e}$s, $R^{10e}$s or $R^{12e}$s), the $R^{6e}$s (or $R^{8e}$s, $R^{10e}$s or $R^{12e}$s) may be the same or different from one another. In other words, the alkylene oxide to be added is ethylene oxide, propylene oxide or a mixture of ethylene oxide with propylene oxide.

Among the compounds of the formula (F) according to the present invention, preferable ones are those wherein $R^{13f}$ is a hydrogen atom, an alkyl group having 1 to 2 carbon atoms or a benzyl group, $R^{14f}$ is a methyl, ethyl or hydroxyethyl group, and $R^{15f}$ and $R^{16f}$ are either the same or different from each other and each represents an alkyl group having 8 to 22 carbon atoms, and still more preferable ones are those wherein $R^{13f}$ is a hydrogen atom or an alkyl group having 1 to 2 carbon atoms, $R^{14f}$ is a methyl, ethyl or hydroxyethyl group, and $R^{15f}$ and $R^{16f}$ are either the same or different from each other and each represents an alkyl group having 8 to 22 carbon atoms.

When used together with an agricultural chemical, the enhancer for agricultural chemicals according to the present invention, i.e., the compound represented by any of the above formulae (A) to (F), can enhance the effectiveness of the agricultural chemical twice or thrice without causing any phytotoxicity. Namely, the enhancer for agricultural chemicals of the present invention can be safely applied to various crops without causing any phytotoxicity.

It has not necessarily been clarified why the enhancer for agricultural chemicals comprising any of the compounds represented by the formulae (A) to (F) according to the present invention exerts a remarkable enhancement effect regardless of the type of the structure of the agricultural chemical. One of the reasons therefor seemingly resides in that the enhancer of the present invention exerts a very strong solubilizing power on an agricultural chemical and, therefore, improves the wettability and permeability of the agricultural chemical, or promotes the penetration of the agricultural chemical into insects, fungi and bacteria.

The combined use of at least one member selected from the group consisting of the compounds represented by the formulae (A) to (F) according to the present invention with surfactant(s) other than these compounds makes it possible to reduce the dose of the compound(s) represented by the formulae (A) to (F) while maintaining their enhancement effect on agricultural chemicals. Namely, the present invention also relates to an enhancer (or an enhancer composition) comprising a compound represented by any of the formulae (A) to (F) and a surfactant other than compounds represented by the formulae (A) to (F).

As surfactants other than the compounds represented by the formulae (A) to (F), nonionic surfactants, anionic surfactants, cationic surfactants, ampholytic surfactants and mixtures of two or more surfactants described above are useful.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkylsorbitol esters, polyoxyalkylene sorbitan esters, polyoxyalkylene alkylglycerol esters, polyoxyalkylene block copolymers, polyoxyalkylene block copolymer/alkylglycerol esters, polyoxyalkylene alkylsulfonamides, polyoxyalkylene rosin esters, polyoxypropylene block copolymers, polyoxyethylene oleyl ethers, polyoxyalkylene alkylphenols, alkylglycosides, alkylpolyglycosides, polyoxyalkylene alkylpolyglycosides, and mixtures comprising two or more of these surfactants.

Examples of the cationic surfactants include alkylamine/ethylene oxide adducts and alkylamine/propylene oxide adducts such as tallow amine/ethylene oxide adduct, oleylamine/ethylene oxide adduct, soy amine/ethylene oxide adduct, coco amine/ethylene oxide adduct, synthetic alkylamine/ethylene oxide adducts, octylamine/ethylene oxide adduct and mixtures thereof.

Among anionic surfactants, typical ones are available in the form of an aqueous solution or a solid. Examples thereof include sodium mono- and dialkylnaphthalenesulfonates, sodium α-olefinsulfonate, sodium alkanesulfonates, alkylsulfosuccinates, alkylsulfates, polyoxyalkylene alkyl ether sulfates, polyoxyalkylene alkyl aryl ether sulfates, polyoxyalkylene styryl phenyl ether sulfates, mono- and dialkylbenzenesulfonates, alkylnaphthalenesulfonates, alkylnaphthalenesulfonate/formaldehyde condensates, alkyl diphenyl ether sulfonates, olefinic sulfonates, mono- and dialkylphosphates, polyoxyalkylene mono- and dialkylphosphates, polyoxyalkylene mono- and diphenyl ether phosphates, polyoxyalkylene mono- and dialkyl phenyl ether phosphates, polycarboxylic acid salts, fatty acid salts, linear and branched alkyl polyoxyalkylene ether acetic acids and salts thereof, linear and branched alkenyl polyoxyalkylene ether acetic acids and salts thereof, stearic acid and its salts, oleic acid and its salts, N-methyl fatty acid taurides and mixtures comprising two or more of these surfactants (including sodium, potassium, ammonium and amine salts).

Examples of suitable ampholytic surfactants include lauryldimethylamine oxide, Armox C/12, amine oxides, Monaterics, Miranols, betaines, Lonzaines, other amine oxides and mixtures thereof.

Among these surfactants, nonionic surfactants are particularly preferable. Still more preferable surfactants include those of the ester type, such as polyoxy-alkylene sorbitan esters and polyoxyalkylene alkyl glycerol esters, polyoxyalkylene alkyl ethers and polyoxyalkylene alkylphenyl ethers.

In an enhancer (or an enhancer composition) for agricultural chemicals comprising the compound(s) represented by the above formulae (A) to (F) and surfactant(s) other than said compounds, the weight ratio of the content of the compound(s) represented by the above formulae (A) to (F) to the content of the surfactant(s), i.e., [the (total) content of the compound(s) represented by the above formulae (A) to (F)/the (total) content of the surfactant(s) other than said compounds], preferably ranges from 1/10 to 50/1, still more preferably from 1/1 to 10/1.

The agricultural chemical composition of the present invention comprises the above-mentioned enhancer and an agricultural chemical. In the agricultural chemical composition comprising the enhancer and an agricultural chemical according to the present invention, it is necessary to use the compound(s) represented by the general formulae (A) to (F), i.e., the enhancer, in an amount wherein the weight ratio of the (total) content of the compound(s) represented by the formulae (A) to (F) to the (total) content of the agricultural chemical(s) is from 0.05 to 50, preferably from 0.05 to 20 and still more preferably from 0.1 to 10. When this ratio is below 0.05, any desired effect of enhancing the effectiveness of the agricultural chemical(s) can not be fully achieved. When this ratio exceeds 50, on the other hand, the enhancing effect is no longer improved.

Next, examples of the agricultural chemicals to be used in the agricultural chemical composition of the present invention will be cited, though the agricultural chemicals to be used in the present invention is not restricted thereto.

In the case of fungicides (or bactericides), included are Zineb [zinc ethylenebis(dithiocarbamate)], Maneb [manganese ethylenebis(dithiocarbamate)], Thiram [bis(dimethylthiocarbamoyl) disulfide], Mancozeb [complex of zinc and manganese ethylenebis(dithiocarbamate)], Polycarbamate [dizinc bis(dimethyldithiocarbamate) ethylenebis(dithiocarbamate)], Propineb [polymeric zinc propylenebis(dithiocarbamate)], benzimidazole fungicides such as Benomyl [methyl]-(butylcarbamoyl)-2-benzimidazolecarbamate] and Thiophanate-methyl [1,2-bis( 3-methoxycarbonyl-2-thioureido)benzene]; Vinclozolin [3-(3,5-dichlorophenyl)-5-methyl-5-vinyl-1,3-oxazolidine-2,4-dione], Iprodione [3-(3, 5-dichlorophenyl)-N-isopropyl- 2,4-dioxoimidazolidine-1-carboxamide], Procymidone [N-(3,5-dichlorophenyl)-1,2-dimethylcyclopropane- 1,2-dicarboximide], Anilazine (Triazine) [2,4-dichloro-6-(2-chloroanilino)-1,3,5-triazine], Triflumizole [(E)-4-chloro-α,α,α-trifluoro-N-( 1-imidazol-1-yl-2-propoxyethylidene)toluidine], Metalaxyl [methyl N-(2-methoxyacetyl)-N-(2,6-xylyl)DL-alaninate], Biter-tanol [all-rac-1-(biphenyl-4-yl-oxy)- 3,3-dimethyl-1-(1H-1, 2,4-triazol-1-yl)-2-butan-2-ol], Pyrifenox [2',4'-dichloro-2-(3-pyridyl)acetophenone (EZ)-O-methyloxime], Fenarimol [2,4'-dichloro-α-(pyridin- 5-yl)benzhydryl alcohol], Trifo-rine [1,4-bis-( 2,2,2-trichloro-1-formamidoethyl)piperazine], Iminoctadine acetate [1,1'-iminiodi(octamethylene)-diguanidinium triacetate], organocopper compound (Oxine-copper [copper 8-quinolinolate]), antibiotic bactericides (streptomycin type, tetracycline type, polyoxins type, blasticidin S, kasugamycin type, validamycin type), Triadimefon [1-(4-chlorophenoxy)-3,3-dimethyl-1-(1,2,4- triazol-1-yl)-2-butanone], Isoprothiolane (diisopropyl 1,3-dithiolan-2-ylidenemalonate], Chlorothaloni](Daconil) [tetrachloroisophthalonitrile], Etridiazol (Pansoil) [5-ethoxy-3-trichloromethyl- 1,2,4-thiadiazole], Fthalide [4,5,6,7-tetrachlorophthalide], Iprobenfos (Kitazin P) [O,O -diisopropyl-S-benzyl thiophosphate], Edifenphos (Hinosan) [O-ethyl S,S-diphenyl dithiophosphate], Probenazole [3-allyloxy-1,2-benzisothiazole-1,1-dioxide], Captan [N-trichloromethylthiotetrahydrophthalimide] and Fosetyl [aluminum tris(ethylphosphonate)].

In the case of insecticides, included are pyrethroid insecticides such as Fenvalerate [α-cyano-3-phenoxybenzyl 2-(4-chlorophenyl)-3-methylbutanoate] and Cyfluthrin (Baythroid) [α-cyano-4-fluoro-3-phenoxyphenylmethyl 3-(2,2-dichloroethenyl)-2,2-dimethylcyclcopropanecarboxylate]; organophosphorus insecticides such as Dichlorvos (DDVP) [dimethyl 2,2-dichlorovinyl phosphate], Fenitrothion (MEP) [O,O -dimethyl-O-(3-methyl-4-nitrophenyl)thiophosphate], Malathion (Malathon) [S-[1,2-bis(ethoxycarbonyl)ethyl] dimethyl phosphorothiol-thionate], Dimethoate [dimethyl S-(N-methylcarbamoylmethyl)-dithiophosphate], Phenthoate (Elsan) [S-[α-(ethoxycarbonyl)benzyl]dimethyl phosphorothiol-thionate] and Fenthion (Baycid) [O,O -dimethyl-O-[3-methyl-4-(methylthio)phenyl]thiophosphate]; carbamate insecticides such as Fenobucarb (Bassa) [O-sec-butylphenyl methylcarbamate], Metolcarb (MTMC) [m-tolyl methylcarbamate], Xylylcarb (Meobal) [3,4-dimethylphenyl N-methylcarbamate] and Carbaryl (NAG) [1-naphthyl N-methylcarbamate]; Methomyl [S-methyl N-(methylcarbamoyloxy)thioacetimidate] and Cartap [1,3-bis(carbamoylthio)-2-(N,N-dimethylamino)propane hydrochloride].

In the case of miticides (or acaricides), included are Pyridaben [2-tert-butyl-5-(4-tert-butylbenzylthio)- 4-chloropyridazin-3(2H)-one], Acricid [2,4-dinitro-6-sec-butylphenyldimethylacrylate], Chloromite [isopropyl 4,4-dichlorobenzylate], Chlorobenzilate (Akar) [ethyl 4,4'-dichlorobenzilate], Dicofol (Kelthane) [1,1-bis(p-chlorophenyl)-2,2,2-trichloroethanol], Benzoximate (Citrazon) [ethyl-O-benzoyl- 3-chloro-2,6-dimethoxybenzohydroximate], Propargite (Omite) [2-(p-tert-butylphenoxy)cyclohexyl 2-propynyl sulfite], Fenbutatin Oxide (Osadan) [hexakis(β,β-dimethylphenylethyl)distannoxane], Hexythiazox [trans-5-(4-chlorophenyl)-N-cyclohexyl-4-methyl-2-oxothiazolidine-3-carboxamide] and Amitraz [3-methyl-1,5-bis(2,4-xylyl)-1,3,5-triazapenta-1,4-diene].

In the case of herbicides, included are acid amide hebicides such as Propanil (DCPA) [3',4'-dichloropropionanilide] and Alachlor [2-chloro-2', 6'-diethyl-N-(methoxyethyl)acetanilide]; urea herbicides such as Diuron (DCMU) [3-(3,4-dichlorophenyl)-1,1-dimethylurea] and Linuron [3-(3,4-dichlorophenyl)-1-methoxy- 1-methylurea); dipyridyl herbicides such as Paraquat Dichloride (Paraquat) [1,1'-dimethyl-4,4'-bipyridirium dichloride] and Diquat Dibromide (Diquat) [6,7-dihydrodipyrido[1,2-a:2', 1'-c]-pyrazindiium dibromide]; diazinc herbicides such as Bromacil [5-bromo- 3-sec-butyl-6-methyluracil]; S-triazine herbicides such as Simazine [2-chloro-4,6-bis(ethylamino)-1,3,5-triazine] and Simetryn [2,4-bis(ethylamino)- 6-methylthio-]1,3,5-triazine]; nitrile herbicides such as Dichlobeni (DBN) [2,6-dichlorobenzonitrile]; dinitroaniline herbicides such as Trifluralin [α,α,α-trifluoro-2,6-dinitro-N,N-dipropyl-p-toluidine]; carbamate herbicides such as Benthiocarb [S-p-chlorobenzyl diethylthiocarbamate] and MCC [methyl 3,4-dichlorocarbanilate]; diphenylether herbicides such as Nitrofen (NIP) [2,4-dichlorophenyl-p-nitrophenylether]; phenol herbicides such as PCP [pentachlorophenol]; benzoic acid herbicides such as Dicamba (MDBA) [3,6-dichloro-2-methoxybenzoic acid dimethylamine salt]; phenoxy herbicides such as 2,4-D [2,4-dichlorophenoxyacetic acid and salts (sodium, amine and ethylether) thereof], and Mapica (MCPCA) [2'-chloro-2-(4-chloro-o-tolyloxy)acetanilide]; organic phosphorus herbicides such as Glyphosate [N-(phosphonomethyl)glycine] and salts thereof, Bialaphos [sodium salt of L-2-amino-4-[(hydroxy)(methyl)phosphinoyl]butyryl-L-alanyl-L-alanine] and Glufosinate [ammonium DL-homoalanin-4-yl (methyl)phosphinate], and aliphatic herbicides such as TCA [trichloroacetic acid and salts thereof].

In the case of plant growth regulators, included are MH (maleic hydrazide), Ethephon [2-chloroethylphosphonic acid], UASTA and Bialaphos.

The agricultural chemical composition of the present invention may be formulated into any preparation such as emulsions, wettable powders, granules, powders and flowables without any limitation. Accordingly, the composition of the present invention may contain other additives which are selected depending on the formulation, for example, emulsifiers, dispersing agents and carriers.

The agricultural chemical composition according to the present invention may further contain a chelating agent, a pH regulator, an inorganic salt or a thickener, if required.

Examples of chelating agents include aminopolycarboxylic acid type chelating agents, aromatic or aliphatic carboxylic acid type chelating agents, amino acid type chelating agents, ether polycarboxylic acid type chelating agents, phosphonic acid type chelating agents such as iminodimethylphosphonic acid (IDP) and alkyldiphosphonic acids (ADPA), and dimethylglyoxime (DG). These chelating agents are as such or in the form of salts (sodium, potassium or ammonium salt) thereof.

Examples of zhe aminopolycarboxylic acid type chelating agents include a) compounds represented by the chemical formula of $RNX_2$, b) compounds represented by the chemical formula of $NX_3$, c) compounds represented by the chemical formula of $R—NX—CH_2CH_2—NX—R$, d) compounds represented by the chemical formula of $R—NX—CH_2CH_2—NX_2$, e) compounds represented by the chemical formula of $X_2N—R'—NX_2$ and f) compounds similar to compounds of e) and containing four or more Xs, for example, a compound represented by the formula:

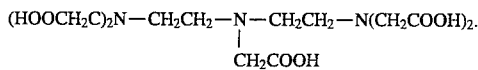

In the above Formulae, X represents $—CH_2COOH$ or $—CH_2CH_2COOH$, R represents a group to be contained in these type, known chelating agents such as a hydrogen atom, an alkyl group, a hydroxyl group and a hydroxyalkyl group, and R' represents a group to be contained in these type, known chelating agents such as an alkylene group and a cycloalkylene group.

Representative examples of the aminopolycarboxylic acid type chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH) and glycoletherdiaminetetraacetic acid (GEDTA), and salts thereof.

Examples of the aromatic or aliphatic carboxylic acid type chelating agents to be used in the present invention include citric acid, oxalic acid, glycolic acid, pyruvic acid and anthranilic acid, and salts thereof. Further, examples of the amino acid type chelating agents to be used in the present invention include glycine, serine, alanine, lysine, cystine, cysteine, ethionine, tyrosine and methionine, and salts and derivatives thereof.

Furthermore, examples of the ether polycarboxylic acid type chelating agents to be used in the present invention include compounds represented by the following formula, compounds similar to the compounds represented by the following formula and salts (e.g., sodium salt) thereof:

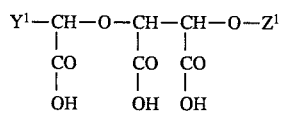

wherein $y^1$ represents a hydrogen atom, $—CH_2COOH$ or $—COOH$, and $Z^1$ represents a hydrogen atom, $—CH_2COOH$ or

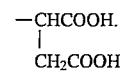

Examples of the pH regulators to be used in the present invention include citric acid, phosphoric acid (e.g., pyrophosphoric acid) and gluconic acid, and salts thereof.

Examples of the inorganic acid salts to be used in the present invention include inorganic mineral salts such as clay, talc, bentonire, zeolite, calcium carbonate, diatomaceous earth and white carbon, and inorganic ammonium salts such as ammonium sulfate, ammonium nitrate, ammonium phosphate, ammonium thiocyanate, ammonium chloride and ammonium sulfamate.

In addition, examples of thickeners to be used in the present invention include natural, semisynthetic and synthetic, water-soluble thickeners. As natural mucilaginous matters, xanthane gum and zanflow, which are derived from microorganism, and pectine, gum arabic and guar gam, which are derived from plant, are cited. As semisynthetic mucilaginous matters, methylated, carboxyalkylated and hydroxyalkylated products of cellulose such as methylcellulose, carboxymethylcellulose and hydroxymethylcellulose, methylated, carboxyalkylated and hydroxyalkylated products of starch derivatives, and sorbitol are cited. Furthermore, polyacrylates, polymaleates, polyvinylpyrrolidone and oentaerythritol/ethyleneoxide adducts are cited as synthetic mucilaginous matters.

The agricultural chemical composition of the present invention may further contain one or more ingredients such as plant growth regulators other than those cited above fertilizers and preservatives.

The agricultural chemical composition of the present invention is used in order to control fungi (or bacteria), insects, mites (or acarids) and herbs or to regulate the growth of plants.

The agricultural chemical kit according to the present invention comprises a container containing the enhancer according to the present invention and another container containing an agricultural chemical composition. In this case, the enhancer may comprise at least one compound represented by the above formulae (A) to (F), or a mixture of at least one compound represented by the above formulae (A) to (F) and at least one surfactant other than the compounds represented by the above general formulae (A) to (F). Alternatively, another agricultural chemical kit according to the present invention comprises a container containing at least one compound represented by the above formulae (A) to (F), a container containing at least one surfactant other than the compounds represented by the above formulae (A) to (F) and a container containing an agricultural chemical composition.

The "agricultural chemical composition" which is a constituent of the kit is a composition which comprises an agricultural chemical(s), is free from the compounds represented by the above formulae (A) to (F) and is in the form of, for example, an emulsion, a liquid or a wettable powder.

In the agricultural chemical kit according to the present invention, a composition comprising an agricultural chemical is separated from the compounds represented by the above Formulae (A) to (F). Namely, the kit differs from an agricultural chemical composition comprising the enhancer for agricultural chemicals and an agricultural chemical(s) in admixture.

Each of contents in these containers is not restricted in their form but appropriately prepared depending on the use and purpose. The material of the container is not restricted so long as it does not react with or affect the content. Examples of the material include plastics, glass, foil, etc.

The enhancer according to the present invention is applied with an agricultural chemical to a locus which would benefit from such treatment, i.e., the application of the enhancer and the agricultural chemical. In general, the enhancer and the agricultural chemical are used with water or a liquid carrier. As means for applying the enhancer for agricultural chemicals according to the present invention, (1) one wherein an agricultural chemical composition of the present invention containing the enhancer and having a preparation form is used (if necessary, the agricultural chemical composition is diluted with, for example, tap water), (2) another one wherein an enhancer is added to an agricultural chemical composition, which has been diluted with water, and (3) another one wherein an enhancer is diluted with water and then an agricultural chemical composition is diluted with the resultant diluted enhancer solution, are useful. The desired enhancement effect can be achieved by either means.

The agricultural chemical composition of the present invention includes one containing the agricultural chemical in high concentration and the enhancer in high concentration, and another one containing the agricultural chemical in an appropriate concentration for application and the enhancer in an appropriate concentration for application. When the former is used, the agricultural chemical composition is diluted with water, etc., for example, just before applying. On the other hand, the agricultural chemical compositions used in the above cases (2) and (3) include those containing the agricultural chemical in high concentration and being free from the enhancer of the present invention.

The contents of the agricultural chemical and the enhancer in their diluted solution are not limited. The content of the agricultural chemical in its diluted solution depends on, for example, the kind of the agricultural chemical and its use. While the content of the enhancer in its diluted solution depends on, for example, the kind of the agricultural chemical to be mixed.

The diluted liquid comprising an appropriate amount of an agricultural chemical and an appropriate amount of an enhancer of the present invention is applied to, for example, plants, crops, vegetables, fruits, trees, fruit trees, grasses, weeds or seeds, and, at the same time, to fungi, bacteria, insects, acarids or mites. In other words, the diluted liquid is applied to a farm, a plantation, a fruit garden, an orchard, a flower garden, a lawn, a wood and a forest.

EXAMPLES

The present invention will now be described in more detail with reference to the following Examples which should not be considered to limit the scope of the present invention.

Example 1

By using compounds listed in Table 1, various enhancers for agricultural chemicals listed in Tables 2 and 3 were prepared.

The above-mentioned enhancers were each dissolved in deionized water to give a 0.2% by weight [as a content of an active ingredient(s)] dilution. With the use of the 0.2% by weight dilution thus obtained, commercially available herbicides, i.e., a Roundup liquid formulation (containing 41% by weight of isopropylamine salt of Glyphosate as an active ingredient), a Karmex wettable powder (containing 78.5% by weight of DCMU as an active ingredient) and Herbiace water-soluble powder (containing 20% by weight of Bialaphos as an active ingredient) were each diluted 300-fold. Thus three agricultural chemical compositions were obtained for each enhancer for agricultural chemicals.

Fertile soil obtained from a paddy field, gravels (i.e., river sand) and a culture soil available on the market were mixed one another at the weight ratio of 7:2:1. Pots having an inside diameter of 12 cm were filled with the soil thus obtained. In order to conduct a glasshouse test, the seeds of crabgrass were sowed in the pots and germinated. The pots wherein the growth of the crabglass was abnormal were abandoned to reduce the irregularity among pots. The pots wherein crabgrasses had been grown at a height of about 18 cm were used in the test. Spray gun (mf. by Iwata Tosoki Kogyo K.K., type RG) was used for the application of the agricultural chemical compositions to the crabgrasses. The crabgrasses in the pots were uniformly sprayed with each of the agricultural chemical compositions at a ratio corresponding to 1000 l/ha (liter per hectare) to evaluate the herbicidal efficacy.

On the tenth day after the application, the above-ground part of the fresh plant was weighed and the result was expressed in a herbicidal percentage on the basis of the fresh weight of the above-ground part in the untreated lot (see the following formula).

$$\text{Herbicidal percentage (\%)} = \frac{\text{above-ground fresh weight (g) of an untreated lot} - \text{above-ground fresh weight (g) of a test lot}}{\text{above-ground fresh weight (g) of an untreated lot}} \times 100$$

Tables 4 and 5 show the herbicidal percentages of the agricultural chemical compositions.

TABLE 1

| Compd. No. | Structure |
|---|---|
| (1) | CH$_3$—N$^+$(CH$_3$)(CH$_3$)—CH$_2$—CH(O—CO—C$_9$H$_{19}$)—CH$_2$—NH—CO—C$_9$H$_{19}$·Cl$^-$ |
| (2) | CH$_3$—N$^+$(CH$_3$)(CH$_3$)—CH$_2$—CH(O—CO—C$_{18}$H$_{35}$)—CH$_2$—NH—CO—C$_{18}$H$_{35}$·C$_2$H$_5$SO$_4^-$ |
| (3)* | CH$_3$—N$^+$(CH$_3$)(H)—CH$_2$—CH(O—CO—C$_7$H$_{15}$)—CH$_2$—O—CO—C$_{11}$H$_{23}$·Cl$^-$ |

TABLE 1-continued

| Compd. No. | Structure |
|---|---|
| (4) | CH₃—N⁺(CH₃)(CH₃)—CH₂—CH(O—CO—C₉H₁₉)—CH₂—NH—CO—C₉H₁₉·Cl⁻ |
| (5) | CH₃—N⁺(CH₃)(CH₂C₆H₅)—CH₂—CH(O—(CH₂CH₂O)₁₀—CO—C₁₁H₂₃)—CH₂—O—(CH₂CH₂O)₁₀—CO—C₁₁H₂₃·Cl⁻ |
| (6) | CH₃—N⁺(CH₃)(H)—CH₂—CH(O—CO—C₁₇H₃₅)—CH₂—O—C₁₈H₃₇·CH₃COO⁻ |
| (7) | H—(OCH₂CH₂)₃—N⁺(CH₃)(CH₃)—CH₂—CH(O—CO—C₉H₁₉)—CH₂—NH—CO—C₉H₁₉·Cl⁻ |

Note:
*Compound (3) is a mixture of the compound described in the above Table with the following compound at a weight ratio of about 1:1.

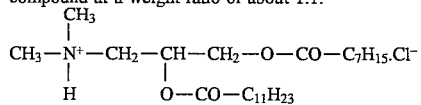

CH₃—N⁺(CH₃)(H)—CH₂—CH(O—CO—C₁₁H₂₃)—CH₂—O—CO—C₇H₁₅·Cl⁻

TABLE 2

| Enhancer No. | Compd. No. (A) | Surfactant (B) used together | (A)/(B) by wt. |
|---|---|---|---|
| 1 | (1) | — | 100/0 |
| 2 | (1) | POE(10) nonylphenyl ether | 80/20 |
| 3 | (1) | POE(7) sec. C₁₂₋₁₃ ether | 80/20 |
| 4 | (1) | POE(20) sorbitan monooleate | 80/20 |
| 5 | (2) | — | 100/0 |
| 6 | (2) | POE(9) nonylphenyl ether | 75/25 |
| 7 | (2) | POE(7) linear & branched C₁₂₋₁₃ ether | 75/25 |
| 8 | (2) | POE(20) sorbitan monolaurate | 75/25 |
| 9 | (3) | — | 100/0 |
| 10 | (3) | POE(10) nonylphenyl ether | 80/20 |
| 11 | (3) | POE(7) sec. C₁₂₋₁₃ ether | 80/20 |
| 12 | (3) | POE(20) sorbitan monooleate | 70/30 |
| 13 | (4) | — | 100/0 |
| 14 | (4) | sodium POE(20) lauryl ether sulfate | 75/25 |
| 15 | (4) | POE(7) sec. C₁₂₋₁₃ ether | 75/25 |
| 16 | (4) | POE(20) sorbitan monolaurate | 75/25 |

Note:
In the above table, POE stands for polyoxyethylene and numbers given in parentheses mean the average addition mole numbers of ethylene oxide (the same will apply hereinafter).

TABLE 3

| Enhancer No. | Compd. No. (A) | Surfactant (B) used together | (A)/(B) by wt. |
|---|---|---|---|
| 17 | (5) | — | 100/0 |
| 18 | (5) | POE(10) nonylphenyl ether | 70/30 |
| 19 | (5) | POE(7) linear & brached C₁₂₋₁₃ ether | 70/30 |
| 20 | (5) | POE(20) sorbitan monooleate | 70/30 |
| 21 | (6) | — | 100/0 |
| 22 | (6) | POE(9) nonylphenyl ether | 80/20 |
| 23 | (6) | POE(7) sec. C₁₂₋₁₃ ether | 80/20 |
| 24 | (6) | POE(20) sorbitan monolaurate | 80/20 |
| 25 | (7) | — | 100/0 |
| 26 | (7) | POE(10) nonylphenyl ether | 80/20 |
| 27 | (7) | POE(7) linear & branched C₁₂₋₁₃ ether | 80/20 |
| 28 | (7) | POE(20) sorbitan monooleate | 80/20 |
| 29 | dimethyldipalmitylammonium chloride | | — |
| 30 | trimethylmonolaurylammonium chloride | | — |
| 31 | monomethyldistearylhydroxyethylammonium chloride | | — |
| 32 | trimethylcocoylammonium chloride | | — |

Note: Enhancer Nos. 29 to 32 are comparative ones.

TABLE 4

| Enhancer No. | Herbicidal percentage (%) | | |
|---|---|---|---|
| | Karmex wettable powder | Herbiace water-soluble powder | Roundup liquid formulation |
| Invention product | | | |
| 1 | 96.3 | 99.0 | 98.4 |
| 2 | 97.2 | 98.2 | 99.1 |
| 3 | 99.1 | 99.2 | 96.8 |
| 4 | 93.1 | 97.4 | 98.2 |
| 5 | 95.7 | 97.6 | 99.4 |
| 6 | 96.8 | 98.3 | 96.5 |
| 7 | 92.3 | 98.7 | 98.7 |
| 8 | 94.9 | 97.0 | 99.0 |
| 9 | 83.4 | 92.9 | 96.2 |
| 10 | 90.6 | 94.3 | 97.7 |
| 11 | 92.8 | 97.8 | 98.4 |
| 12 | 97.7 | 95.4 | 94.1 |
| 13 | 97.8 | 98.8 | 99.3 |
| 14 | 99.3 | 99.2 | 99.5 |
| 15 | 96.9 | 99.1 | 98.8 |
| 16 | 98.4 | 98.7 | 98.2 |

TABLE 5

| Enhancer No. | Herbicidal percentage (%) | | |
|---|---|---|---|
| | Karmex wettable powder | Herbiace water-soluble powder | Roundup liquid formulation |
| Invention product | | | |
| 17 | 98.2 | 96.3 | 99.6 |
| 18 | 95.6 | 93.7 | 99.2 |
| 19 | 89.3 | 97.2 | 98.6 |
| 20 | 92.1 | 98.5 | 98.8 |
| 21 | 97.6 | 95.9 | 91.3 |
| 22 | 98.7 | 97.3 | 95.6 |
| 23 | 99.3 | 99.1 | 96.4 |
| 24 | 98.4 | 98.6 | 99.1 |
| 25 | 95.4 | 99.4 | 98.9 |
| 26 | 97.6 | 98.7 | 99.4 |
| 27 | 97.7 | 99.2 | 99.0 |
| 28 | 98.4 | 99.2 | 98.1 |
| Comp. product | | | |
| 29 | 60.1 | 73.8 | 75.8 |
| 30 | 48.2 | 71.8 | 70.1 |
| 31 | 63.8 | 76.2 | 73.2 |
| 32 | 55.3 | 72.9 | 71.5 |
| no addition | 41.2 | 64.7 | 65.3 |

Example 2

Female imagines of *Tetranychus kanzawai kishida* were planted onto kidney bean leaf discs at a ratio of imagines per lot on 3 runs and then incubated at 25° C. for 24 hours. Subsequently, the whole leaf discs were dipped in a test solution for 5 seconds. After taking out of the test solution and allowing to stand at 25° C. for 48 hours, the leaf discs were observed and the miticidal ratio was determined on the basis of the result in the untreated lot (see the following formula).

$$\text{Miticidal ratio (\%)} = \frac{\text{the number of living mites of an untreated lot} - \text{the number of living mites of a test lot}}{\text{the number of living mites of an untreated lot}} \times 100$$

As miticides, a Nissorun V emulsion (containing 55% by weight of active ingredients including 50% by weight of hexythiazox and 5% by weight of DDVP) and an Osadan wettable powder-25 (containing 25% by weight of phenbutatin oxide as active ingredient) were each diluted 2,000-fold and used. The same enhancers for agricultural chemicals, as those employed in Example 1 were used. The concentration of the active ingredient(s) of each enhancers for agricultural chemicals in the dilution was adjusted to 0.1% by weight. Further, the above procedure was repeated without using any enhancers. Table 6 shows the results.

TABLE 6

| Enhancer No. | Miticidal ratio (%) | |
|---|---|---|
| | Nissolan V emulsion | Osadan wettable powder-25 |
| Invention product | | |
| 1 | 98.9 | 100 |
| 2 | 100 | 97.8 |
| 3 | 100 | 100 |
| 4 | 97.8 | 96.7 |
| 5 | 100 | 92.2 |
| 6 | 96.7 | 96.7 |
| 7 | 97.8 | 100 |
| 8 | 97.8 | 95.6 |
| 9 | 90.0 | 93.3 |
| 10 | 92.2 | 95.6 |
| 11 | 93.3 | 90.0 |
| 12 | 96.7 | 97.8 |
| 13 | 100 | 100 |
| 14 | 98.9 | 100 |
| 15 | 100 | 98.9 |
| 16 | 100 | 96.7 |
| 17 | 92.2 | 96.7 |
| 18 | 97.8 | 98.9 |
| 19 | 97.8 | 93.3 |
| 20 | 98.9 | 95.6 |
| 21 | 93.3 | 92.2 |
| 22 | 90.0 | 95.6 |
| 23 | 96.7 | 97.8 |
| 24 | 90.0 | 93.3 |
| 25 | 98.9 | 100 |
| 26 | 100 | 96.7 |
| 27 | 98.9 | 93.3 |
| 28 | 97.8 | 97.8 |
| Comp. product | | |
| 29 | 50.0 | 46.7 |
| 30 | 48.9 | 51.1 |
| 31 | 50.0 | 44.4 |
| 32 | 48.9 | 53.3 |
| no addition | 43.3 | 42.2 |

Example 3

Rice planthopper larvae of the third instar were incubated and used in an efficacy test on insecticides in triplicate runs by the dipping method (each lot having 10 larvae). The insecticidal ratio was determined in the same manner as the one employed for the determination of the miticidal ratio. Commercially available insecticides, i.e., a Sumithion emulsion (containing 50% by weight of MEP as active ingredient) and a Malathon emulsion (containing 50% by weight of malathon as active ingredient) were each diluted 2,000-fold and used. As enhancers for agricultural chemicals, those employed in Example 1 were used in such a manner as to adjust the concentration of the active ingredient(s) of each enhancer in the diluted solution to 0.1% by weight. Table 7 shows the results.

TABLE 7

| Enhancer No. | Insecticidal ratio (%) | |
|---|---|---|
| | Sumithion emulsion | Malathon emulsion |
| Invention product | | |
| 1 | 100 | 93.3 |
| 2 | 96.7 | 90.0 |
| 3 | 90.0 | 96.7 |
| 4 | 100 | 96.7 |
| 5 | 93.3 | 100 |
| 6 | 100 | 93.3 |
| 7 | 96.7 | 90.0 |
| 8 | 90.0 | 93.3 |
| 9 | 86.7 | 96.7 |
| 10 | 90.0 | 93.3 |
| 11 | 96.7 | 93.3 |
| 12 | 93.3 | 90.0 |
| 13 | 93.3 | 100 |
| 14 | 100 | 96.7 |
| 15 | 100 | 93.3 |
| 16 | 96.7 | 100 |
| 17 | 90.0 | 90.0 |
| 18 | 93.3 | 96.7 |
| 19 | 86.7 | 86.7 |
| 20 | 93.3 | 90.0 |
| 21 | 96.7 | 93.3 |
| 22 | 93.3 | 93.3 |
| 23 | 90.0 | 100 |
| 24 | 96.7 | 90.0 |
| 25 | 100 | 96.7 |
| 26 | 96.7 | 100 |
| 27 | 86.7 | 96.7 |
| 28 | 90.0 | 93.3 |
| Comp. product | | |
| 29 | 63.3 | 56.7 |
| 30 | 53.3 | 60.0 |
| 31 | 53.3 | 63.3 |
| 32 | 50.0 | 60.0 |
| no addition | 43.3 | 50.0 |

Example 4

10 ml/pot of a spore suspension ($10^7$ spores/ml) of *Botrytis cinenea* acquiring the resistance against fungicides was applied onto young cucumber seedlings with 3 true leaves, which were then allowed to stand at 25° C. under a relative humidity of 90% for 1 day.

Then, a commercially available fungicide, i.e., a Benlate wettable powder (containing 50% by weight of benomyl as active ingredient), was diluted 2000-fold with the 2500-dilution of each enhancer employed in Example 1. The dilution thus obtained was applied onto the seedlings at a ratio of 5 ml/pot. After allowing to stand at 25° C. under a relative humidity of 85%, lesions were counted and the preventive value was calculated in accordance with the following formula. Table 8 shows the results.

$$\text{Preventive value} = \left(1 - \frac{\text{no. of lesions of a test lot}}{\text{no. of lesions of an untreated lot}}\right) \times 100$$

TABLE 8

| Enhancer No. | Preventive value Benlate wettable powder |
|---|---|
| Invention product | |
| 1 | 98 |
| 2 | 100 |
| 3 | 95 |
| 4 | 98 |
| 5 | 93 |
| 6 | 98 |
| 7 | 100 |
| 8 | 98 |
| 9 | 95 |
| 10 | 93 |
| 11 | 95 |
| 12 | 100 |
| 13 | 100 |
| 14 | 100 |
| 15 | 95 |
| 16 | 98 |
| 17 | 95 |
| 18 | 93 |
| 19 | 95 |
| 20 | 95 |
| 21 | 98 |
| 22 | 93 |
| 23 | 95 |
| 24 | 93 |
| 25 | 100 |
| 26 | 93 |
| 27 | 90 |
| 28 | 98 |
| Comp. product | |
| 29 | 63 |
| 30 | 70 |
| 31 | 75 |
| 32 | 70 |
| no addition | 60 |

The above Examples 1 to 4 show tests whereby the efficacies of the enhancers for agricultural chemicals of the present invention were compared with those of common cationic surfactants (comparative products) employed as enhancers for agricultural chemicals. As Tables 4 to 11 clearly indicate, the enhancers for agricultural chemicals of the present invention exerted remarkable effects and thus were usable on a practical level. In contrast, the comparative products somewhat enhanced the efficacies of the agricultural chemicals but were not effective on a practical level. Accordingly, it is observed that the enhancers for agricultural chemicals of the present invention would specifically enhance the efficacies of agricultural chemicals as compared with common cationic surfactants.

Example 5

The same test as the one effected in Example 1 was carried out by using a Roundup liquid formulation (containing 41% by weight of active ingredient) as a herbicide, and the enhancers 7, 14 and 17 of Example 1 as enhancers each in the amount as specified in Table 9. The results are given in Table 9. In Table 9, the term "agricultural chemical concentration" stands for the concentration of the active ingredient(s) of the commercially available agricultural chemical formulation in the dilution for application, and the term "enhancer concentration" stands for the concentration of the active ingredient(s) of the enhancer in the dilution for application (the same will apply hereinafter).

TABLE 9

| Test No. | En-hancer No. | Herbicide concn. (ppm) | Enhancer concn. (ppm) | Agricultural chemical concn./ enhancer concn. by wt. | Herbicidal percentage (%) |
|---|---|---|---|---|---|
| 1 | 7 | 2000 | 50 | 1/0.06 | 87.6 |
| 2 |   | 2000 | 100 | 1/0.12 | 95.3 |
| 3 |   | 2000 | 500 | 1/0.6 | 98.6 |
| 4 |   | 2000 | 1000 | 1/1.2 | 99.2 |
| 5 |   | 2000 | 5000 | 1/6 | 97.7 |
| 6 |   | 2000 | 10000 | 1/12 | 98.8 |
| 7 |   | 2000 | 30000 | 1/37 | 99.0 |
| 8 | 14 | 2000 | 50 | 1/0.06 | 88.3 |
| 9 |   | 2000 | 100 | 1/0.12 | 93.8 |
| 10 |   | 2000 | 500 | 1/0.6 | 98.9 |
| 11 |   | 2000 | 1000 | 1/1.2 | 96.7 |
| 12 |   | 2000 | 5000 | 1/6 | 99.1 |
| 13 |   | 2000 | 10000 | 1/12 | 98.2 |
| 14 |   | 2000 | 30000 | 1/37 | 98.5 |
| 15 | 17 | 2000 | 50 | 1/0.06 | 90.6 |
| 16 |   | 2000 | 100 | 1/0.12 | 97.3 |
| 17 |   | 2000 | 500 | 1/0.6 | 95.4 |
| 18 |   | 2000 | 1000 | 1/1.2 | 98.6 |
| 19 |   | 2000 | 5000 | 1/6 | 97.7 |
| 20 |   | 2000 | 10000 | 1/12 | 98.9 |
| 21 |   | 2000 | 30000 | 1/37 | 97.9 |
| 22 | — | 2000 | 0 | — | 57.3 |

Example 6

The same test as the one effected in Example 3 was carried out by using a Sumithion emulsion as an insecticide, and the enhancers 5 and 16 of Example 1 as enhancers each in the amount as specified in Table 10. The results are given in Table 10.

TABLE 10

| Test No. | En-hancer No. | Insecticide concn. (ppm) | Enhancer concn. (ppm) | Agricultural chemical concn./ enhancer concn. by wt. | Insecticidal ratio (%) |
|---|---|---|---|---|---|
| 1 | 5 | 250 | 10 | 1/0.08 | 83.3 |
| 2 |   | 250 | 25 | 1/0.2 | 90.0 |
| 3 |   | 250 | 250 | 1/2 | 96.7 |
| 4 |   | 250 | 1000 | 1/8 | 100 |
| 5 |   | 250 | 2500 | 1/20 | 100 |
| 6 |   | 250 | 5000 | 1/40 | 100 |
| 7 | 16 | 250 | 10 | 1/0.08 | 86.7 |
| 8 |   | 250 | 25 | 1/0.2 | 93.3 |
| 9 |   | 250 | 250 | 1/2 | 93.3 |
| 10 |   | 250 | 1000 | 1/8 | 100 |
| 11 |   | 250 | 2500 | 1/20 | 100 |
| 12 |   | 250 | 5000 | 1/40 | 100 |
| 13 | — | 250 | 0 | — | 57.3 |

Production Examples 150 g of a 50% aqueous solution of dimethylamine was introduced into a four-necked flask provided with a stirrer, a thermometer and a dropping funnel. 115 g of glycerol-α-monochlorohydrin and 95 g of a 48% aqueous solution of sodium hydroxide were dropwise added thereinto under cooling and the resulting mixture was stirred under cooling for 10 hours. The obtained aqueous solution was distilled at 80° C. under reduced pressure to remove water. The residue was distilled to thereby give 100 g of dimethylaminopropanediol (A) as distillate.

40 g of the compound (A) obtained above and 275 g of polyoxyethylene ether carboxylic acid were introduced into a four-necked flask provided with a stirrer, a thermometer and a dehydrating tube and the mixture was heated to 180° C. Esterification was effected at the same temperature for 10 hours while removing the water thus formed by distillation. Thus 300 g of the compound (11) was obtained.

Example 11

By using compounds listed in Table 11, various enhancers for agricultural chemicals listed in Table 12 were prepared.

The above-mentioned enhancers were each dissolved in deionized water to give a 0.24 by weight [as a content of an active ingredient(s)] dilution. With the use of the 0.2% by weight dilution thus obtained, commercially available herbicides, i.e., a Roundup liquid formulation (containing 41% by weight of isopropylamine salt of Glyphosate as an active ingredient), a Karmex wettable powder (containing 78.5% by weight of DCMU as an active ingredient) and Herblace water-soluble powder (containing 20% by weight of Bialaphos as an active ingredient) were each diluted 300-fold. Thus three agricultural chemical compositions were obtained for each enhancer for agricultural chemicals.

The same test as the one effected in Example 1 was carried out by using the agricultural chemical compositions thus prepared, and the herbicidal percentages were calculated in the same manner as that described in Example 1.

Table 13 shows the herbicidal percentages of the agricultural chemical compositions.

TABLE 11

| Compd. No. | Structure |
|---|---|
| (11) | $CH_3\diagdown$ $CH_3\diagup$ $N-CH_2CHCH_2-OCO-CH_2-(OCH_2CH_2)_5-O-C_8H_{17}$ <br> $\qquad\qquad\qquad |$ <br> $\qquad\qquad\qquad OCO-CH_2-(OCH_2CH_2)_5-O-C_8H_{17}$ |
| (12) | $CH_3\diagdown$ $CH_3\diagup$ $N-CH_2CHCH_2-OCO-C_2H_4-(OCH_2CH_2)_{10}-O-C_{12}H_{25}$ <br> $\qquad\qquad\qquad |$ <br> $\qquad\qquad\qquad OCO-C_2H_4-(OCH_2CH_2)_{10}-O-C_{12}H_{25}$ |
| (13)* | $CH_3\diagdown$ $HOC_2H_4\diagup$ $N-CH_2CHCH_2-OCO-C_2H_4-(OCH_2CH_2)_{15}-O-C_{12}H_{25}$ <br> $\qquad\qquad\qquad |$ <br> $\qquad\qquad\qquad OCO-C_2H_4-(OCH_2CH_2)_{15}-O-C_8H_{17}$ |
| (14) | $CH_3\diagdown$ $CH_3\diagup$ $N-CH_2CHCH_2-OCO-CH_2-O-C_{18}H_{35}$ <br> $\qquad\qquad\qquad |$ <br> $\qquad\qquad\qquad OCO-CH_2-O-C_{18}H_{35}$ |

Note:
*Compound (13) is a mixture of the compound described in the above Table with the following compound at a weight ratio of about 1:1.

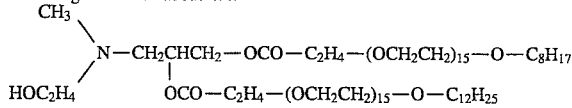

TABLE 12

| Enhancer No. | Compd. No. (A) | Surfactant (B) used together | (A)/(B) by wt. |
|---|---|---|---|
| 101 | (11) | — | 100/0 |
| 102 | (11) | POE(20) sorbitan monooleate | 80/20 |
| 103 | (11) | sodium POE(20) lauryl ether sulfate | 80/20 |
| 104 | (12) | — | 100/0 |
| 105 | (12) | POE(9) nonylphenyl ether | 80/20 |
| 106 | (12) | POE(7) sec. $C_{12-13}$ ether | 80/20 |
| 107 | (13) | — | 100/0 |
| 108 | (13) | POE(10) nonylphenyl ether | 80/20 |
| 109 | (13) | POE(8) oleyl ether | 80/20 |
| 110 | (14) | — | 100/0 |
| 111 | (14) | POE(7) linear & branched $C_{12-13}$ ether | 80/20 |
| 112 | (14) | POE(10) octylphenyl ether | 80/20 |
| 113 | monomethyldilaurylamine | | — |
| 114 | dimethylmonopalmitylamine | | — |
| 115 | POE(3) octylamine | | — |

Note: Enhancer Nos. 113 to 115 are comparatve ones.

TABLE 13

| | Herbicidal percentage (%) | | |
|---|---|---|---|
| Enhancer No. | Karmex wettable powder | Herbiace water-soluble powder | Round up liquid formulation |
| Invention product | | | |
| 101 | 91.2 | 98.3 | 99.5 |
| 102 | 89.3 | 95.1 | 95.4 |
| 103 | 93.1 | 95.7 | 96.2 |
| 104 | 97.8 | 97.5 | 99.9 |
| 105 | 95.1 | 97.7 | 95.6 |
| 106 | 95.1 | 95.6 | 93.2 |
| 107 | 93.7 | 99.0 | 99.7 |
| 108 | 91.2 | 94.2 | 94.8 |
| 109 | 94.8 | 97.2 | 95.0 |
| 110 | 87.6 | 91.3 | 89.7 |
| 111 | 89.5 | 90.8 | 92.1 |
| 112 | 92.3 | 91.8 | 95.1 |
| Comp. product | | | |
| 113 | 49.4 | 62.4 | 68.9 |
| 114 | 53.8 | 68.1 | 70.5 |
| 115 | 63.4 | 72.4 | 76.1 |
| no addition | 42.3 | 60.5 | 63.8 |

Example 12

The same test as the one effected in Example 2 was carried out and the miticidal ratio was determined in the same manner as that described in Example 2, except that the enhancers For agricultural chemicals employed in Example 11 were used.

TABLE 14

| Enhancer No. | Miticidal ratio (%) | |
| --- | --- | --- |
| | Nissolan V emulsion | Osadan wettable powder-25 |
| Invention product | | |
| 101 | 97.3 | 100 |
| 102 | 96.0 | 100 |
| 103 | 95.3 | 98.6 |
| 104 | 100 | 100 |
| 105 | 98.6 | 98.6 |
| 106 | 99.3 | 99.3 |
| 107 | 99.3 | 97.3 |
| 108 | 100 | 100 |
| 109 | 100 | 98.6 |
| 110 | 95.3 | 95.3 |
| 111 | 96.0 | 97.3 |
| 112 | 95.3 | 99.3 |
| Comp. product | | |
| 113 | 51.3 | 46.7 |
| 114 | 60.0 | 48.0 |
| 115 | 66.7 | 53.3 |
| no addition | 46.7 | 43.3 |

Example 13

The same test as the one effected in Example 3 was carried out and the insecticidal ratio was determined in the same manner as that of Example 3, except that the enhancers for agricultural chemicals employed in Example 11 were used.

Table 15 shows the results.

TABLE 15

| Enhancer No. | Insecticidal ratio (%) | |
| --- | --- | --- |
| | Sumithion emulsion | Malathon emulsion |
| Invention product | | |
| 101 | 96.7 | 96.7 |
| 102 | 96.7 | 100 |
| 103 | 96.7 | 100 |
| 104 | 96.7 | 96.7 |
| 105 | 100 | 100 |
| 106 | 96.7 | 100 |
| 107 | 93.3 | 96.7 |
| 108 | 96.7 | 96.7 |
| 109 | 96.7 | 100 |
| 110 | 90.0 | 90.0 |
| 111 | 96.7 | 93.3 |
| 112 | 93.3 | 96.7 |
| Comp. product | | |
| 113 | 46.7 | 53.3 |
| 114 | 50.0 | 56.7 |
| 115 | 63.3 | 66.7 |
| no addition | 43.3 | 46.7 |

Example 14

The same test as the one effected in Example 4 was carried out and the preventive value was determined in the same manner as that described in Example 4, except that the enhancers for agricultural chemicals employed in Example 11 were used.

Table 16 shows the results.

TABLE 16

| Enhancer No. | Preventive value Benlate wettable powder |
| --- | --- |
| Invention product | |
| 101 | 94 |
| 102 | 96 |
| 103 | 96 |
| 104 | 91 |
| 105 | 95 |
| 106 | 93 |
| 107 | 97 |
| 108 | 100 |
| 109 | 99 |
| 110 | 89 |
| 111 | 93 |
| 112 | 92 |
| Comp. product | |
| 113 | 60 |
| 114 | 64 |
| 115 | 71 |
| no addition | 58 |

The above Examples 11 to 14 show tests whereby the efficacies of the enhancers for agricultural chemicals of the present invention were compared with those of common cationic surfactants (comparative products) employed as enhancers for agricultural chemicals. As Tables 13 to 16 clearly indicate, the enhancers for agricultural chemicals of the present invention exerted remarkable effects and thus were usable on a practical level. In contrast, the comparative products somewhat enhanced the efficacies of the agricultural chemicals but were not effective on a practical level. Accordingly, it is observed that the enhancers for agricultural chemicals of the present invention would specifically enhance the efficacies of agricultural chemicals as compared with common cationic surfactants.

Example 15

The same test as the one effected in Example 1 was carried out by using a Roundup liquid formulation (containing 41% by weight of active ingredient) as a herbicide, and the enhancers 101 and 109 of Example 11 as enhancers each in the amount as specified in Table 17. The results are given in Table 17.

TABLE 17

| Test No. | Enhancer No. | Herbicide concn. (ppm) | Enhancer concn. (ppm) | Agricultural chemical concn./ enhancer concn. by wt. | Herbicidal percentage (%) |
| --- | --- | --- | --- | --- | --- |
| 1 | 101 | 2000 | 50 | 1/0.06 | 88.9 |
| 2 | | 2000 | 100 | 1/0.12 | 92.4 |
| 3 | | 2000 | 500 | 1/0.6 | 97.5 |
| 4 | | 2000 | 1000 | 1/1.2 | 99.8 |
| 5 | | 2000 | 5000 | 1/6 | 99.7 |
| 6 | | 2000 | 10000 | 1/12 | 98.6 |
| 7 | | 2000 | 30000 | 1/37 | 98.0 |
| 8 | 109 | 2000 | 50 | 1/0.06 | 87.6 |
| 9 | | 2000 | 100 | 1/0.12 | 89.9 |
| 10 | | 2000 | 500 | 1/0.6 | 94.2 |
| 11 | | 2000 | 1000 | 1/1.2 | 98.0 |

TABLE 17-continued

| Test No. | En- hancer No. | Herbicide concn. (ppm) | Enhancer concn. (ppm) | Agricultural chemical concn./ enhancer concn. by wt. | Herbicidal percentage (%) |
|---|---|---|---|---|---|
| 12 |  | 2000 | 5000 | 1/6 | 98.0 |
| 13 |  | 2000 | 10000 | 1/12 | 97.5 |
| 14 |  | 2000 | 30000 | 1/37 | 97.7 |
| 22 | — | 2000 | 0 | — | 67.1 |

Example 16

The same test as the one effected in Example 3 was carried out by using a Sumithion emulsion as an insecticide, and the enhancers 104 and 111 of Example 11 as enhancers each in the amount as specified in Table 18. The results are given in Table 18.

TABLE 18

| Test No. | En- hancer No. | Insecticide concn. (ppm) | Enhancer concn. (ppm) | Agricultural chemical concn./ enhancer concn. by wt. | Insecticidal ratio (%) |
|---|---|---|---|---|---|
| 1 | 104 | 250 | 10 | 1/0-08 | 86.7 |
| 2 |  | 250 | 25 | 1/0.2 | 90.0 |
| 3 |  | 250 | 250 | 1/2 | 93.3 |
| 4 |  | 250 | 1000 | 1/8 | 96.7 |
| 5 |  | 250 | 2500 | 1/20 | 96.7 |
| 6 |  | 250 | 5000 | 1/40 | 96.7 |
| 7 | 111 | 250 | 10 | 1/0.08 | 86.7 |
| 8 |  | 250 | 25 | 1/0.2 | 93.3 |
| 9 |  | 250 | 250 | 1/2 | 96.7 |
| 10 |  | 250 | 1000 | 1/8 | 96.7 |
| 11 |  | 250 | 2500 | 1/20 | 96.7 |
| 12 |  | 250 | 5000 | 1/40 | 93.3 |
| 13 | — | 250 | 0 | — | 43.3 |

Example 17

By using compounds listed in Table 19, various enhancers for agricultural chemicals listed in Table 20 were prepared.

By using the above-mentioned enhancers, herbicidal efficacies were evaluated in the same manner as that in Example 1. Table 21 shows the herbicidal percentage of the agricultural compositions used.

TABLE 19

| Compd. No. | Structure |
|---|---|
| (15) | $\begin{array}{c}CH_3\\CH_3-\overset{\oplus}{N}-CH_2CHCH_2-OCO-CH_2-(OCH_2CH_2)_3-O-C_8H_{17}\cdot C_2H_5SO_4^{\ominus}\\CH_3\quad\quad\ \ OCO-CH_2-(OCH_2CH_2)_3-O-C_8H_{17}\end{array}$ |
| (16) | $\begin{array}{c}CH_3\\CH_3-\overset{\oplus}{N}-CH_2CHCH_2-OCO-CH_2-(OCH_2CH_2)_5-O-C_{18}H_{35}\cdot Cl^{\ominus}\\H\quad\quad\ \ OCO-CH_2-(OCH_2CH_2)_5-O-C_{18}H_{35}\end{array}$ |
| (17)** | $\begin{array}{c}CH_3\\CH_3-\overset{\oplus}{N}-CH_2CHCH_2-OCO-C_2H_4-(OCH_2CH_2)_5-O-C_{14}H_{19}\cdot Cl^{\ominus}\\CH_2\quad\ OCO-C_2H_4-(OCH_2CH_2)_{10}-O-C_8H_{17}\\|\\C_6H_5\end{array}$ |
| (18) | $\begin{array}{c}CH_3\\CH_3-\overset{\oplus}{N}-CH_2CHCH_2-OCO-CH_2-(OCH_2CH_2)_{10}-O-C_{12}H_{25}\cdot Cl^{\ominus}\\CH_3\quad\quad\ \ OCO-CH_2-(OCH_2CH_2)_{10}-O-C_{12}H_{25}\end{array}$ |

Note:
Compound (17) is a mixture of the compound described in the above Table with the following compound at a weight ratio of about 1:1.

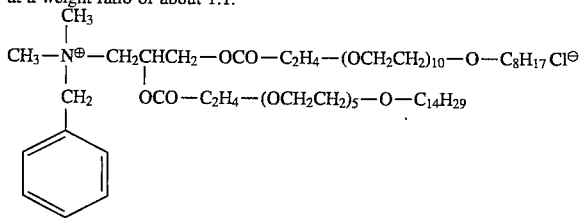

TABLE 20

| Enhancer No. | Compd. No. (A) | Surfactant (B) used together | (A)/(B) by wt. |
|---|---|---|---|
| 116 | (15) | — | 100/0 |
| 117 | (15) | POE(10) nonylphenyl ether | 80/20 |
| 118 | (15) | POE(20) sorbitan monooleate | 80/20 |
| 119 | (16) | — | 100/0 |
| 120 | (16) | POE(8) oleyl ether | 80/20 |
| 121 | (16) | POE(6) sorbitan monooleate | 80/20 |
| 122 | (17) | — | 100/0 |
| 123 | (17) | sodium POE(20) lauryl ether sulfate | 80/20 |
| 124 | (17) | POE(7) linear & branched $C_{12-13}$ ether | 80/20 |
| 125 | (18) | — | 100/0 |
| 126 | (18) | POE(20) sorbitan monolaurate | 80/20 |
| 127 | (18) | sodium POE(20) lauryl ether sulfate | 80/20 |
| 128 | dimethyldipalmitylammonium chloride | | — |
| 129 | trimethylmonolaurylammonium bromide | | — |
| 130 | POE(30) monomethylmonostearyl- ammonium chloride | | — |

Note:
Enhancer Nos. 128 to 130 are comparative ones.

TABLE 21

| | Enhancer No. | Herbicidal percentage (%) | | |
|---|---|---|---|---|
| | | Karmex wettable powder | Herbiace water-soluble powder | Round up liquid formulation |
| Invention product | 116 | 89.4 | 94.8 | 97.1 |
| | 117 | 92.3 | 96.7 | 99.8 |
| | 118 | 91.5 | 97.2 | 99.4 |
| | 119 | 94.8 | 96.4 | 98.1 |
| | 120 | 93.2 | 98.1 | 99.4 |
| | 121 | 95.5 | 98.9 | 98.9 |
| | 122 | 90.1 | 97.3 | 99.0 |
| | 123 | 93.4 | 98.4 | 99.5 |
| | 124 | 92.8 | 97.8 | 98.9 |
| | 125 | 88.9 | 93.2 | 97.6 |
| | 126 | 92.1 | 94.5 | 96.5 |
| | 127 | 91.5 | 95.1 | 99.2 |
| Comp. product | 128 | 59.7 | 63.4 | 69.3 |
| | 129 | 60.5 | 68.2 | 74.1 |
| | 130 | 65.2 | 70.4 | 78.2 |
| no addition | | 42.3 | 60.5 | 63.8 |

Example 18

By using the same ehnancers as those used in Example 17, miticidal efficacies were evaluated in the same manner as the one described in Example 2.

Table 22 shows the results.

TABLE 22

| | Enhancer No. | Miticidal ratio (%) | |
|---|---|---|---|
| | | Nissolan V emulsion | Osadan wettable powder-25 |
| Invention product | 116 | 96.0 | 98.0 |
| | 117 | 99.3 | 99.3 |

TABLE 22-continued

| | Enhancer No. | Miticidal ratio (%) | |
|---|---|---|---|
| | | Nissolan V emulsion | Osadan wettable powder-25 |
| | 118 | 100 | 99.3 |
| | 119 | 98.6 | 97.3 |
| | 120 | 100 | 100 |
| | 121 | 100 | 100 |
| | 122 | 97.3 | 96.7 |
| | 123 | 98.6 | 98.0 |
| | 124 | 97.3 | 99.3 |
| | 125 | 93.3 | 93.3 |
| | 126 | 95.3 | 96.0 |
| | 127 | 96.7 | 97.3 |
| Comp. product | 128 | 53.3 | 46.7 |
| | 129 | 66.7 | 53.3 |
| | 130 | 69.3 | 56.7 |
| no addition | | 46.7 | 43.3 |

Example 19

By using the same enhancers as those used in Example 17, insecticidal efficacies were evaluated in the same manner as the one described in Example 3. Table 23 shows the results.

TABLE 23

| | Enhancer No. | Insecticidal ratio (%) | |
|---|---|---|---|
| | | Sumithion emulsion | Malathon emulsion |
| Invention product | 116 | 96.7 | 96.7 |
| | 117 | 100 | 96.7 |
| | 118 | 100 | 100 |
| | 119 | 96.7 | 100 |
| | 120 | 96.7 | 96.7 |
| | 121 | 93.3 | 93.3 |
| | 122 | 100 | 93.3 |
| | 123 | 96.7 | 96.7 |
| | 124 | 96.7 | 96.7 |
| | 125 | 93.3 | 93.3 |
| | 126 | 90.0 | 100 |
| | 127 | 90.0 | 96.7 |
| Comp. product | 128 | 56.7 | 63.3 |
| | 129 | 66.7 | 66.7 |
| | 130 | 70.0 | 70.0 |
| no addition | | 46.7 | 50.0 |

Example 20

By using the same enhancers as those used in Example 17, fungicidal efficacies were evaluated in the same manner as the one described in Example 4. Table 24 shows the results.

TABLE 24

| | Enhancer No. | Preventive value Benlate wettable powder |
|---|---|---|
| Invention product | 116 | 95 |
| | 117 | 99 |
| | 118 | 98 |
| | 119 | 96 |
| | 120 | 100 |
| | 121 | 100 |
| | 122 | 98 |
| | 123 | 99 |
| | 124 | 100 |
| | 125 | 93 |
| | 126 | 95 |
| | 127 | 98 |

TABLE 24-continued

| | Enhancer No. | Preventive value Benlate wettable powder |
|---|---|---|
| Comp. product | 128 | 62 |
| | 129 | 67 |
| | 130 | 74 |
| no addition addition | | 58 |

Example 21

The same test as the one of Example 17 was effected using a Roundup liquid formulation (containing 41% by weight of active ingredient) as a herbicide, and the enhancers 116 and 121 of Example 17 as enhancers each in the amount as specified in Table 25. The results are given in Table 25.

TABLE 25

| Test No. | Enhancer No. | Herbicide concn. (ppm) | Enhancer concn. (ppm) | Agricultural chemical concn./ enhancer concn. by wt. | Herbicidal percentrage (%) |
|---|---|---|---|---|---|
| 1 | 116 | 2000 | 50 | 1/0.06 | 88.9 |
| 2 | | 2000 | 100 | 1/0.12 | 90.9 |
| 3 | | 2000 | 500 | 1/0.6 | 95.4 |
| 4 | | 2000 | 1000 | 1/1.2 | 99.1 |
| 5 | | 2000 | 5000 | 1/6 | 99.5 |
| 6 | | 2000 | 10000 | 1/12 | 99.4 |
| 7 | | 2000 | 30000 | 1/37 | 99.0 |
| 8 | 121 | 2000 | 50 | 1/0.06 | 93.2 |
| 9 | | 2000 | 100 | 1/0.12 | 96.5 |
| 10 | | 2000 | 500 | 1/0.6 | 97.6 |
| 11 | | 2000 | 1000 | 1/1.2 | 99.1 |
| 12 | | 2000 | 5000 | 1/6 | 99.7 |
| 13 | | 2000 | 10000 | 1/12 | 99.1 |
| 14 | | 2000 | 30000 | 1/37 | 99.0 |
| 22 | — | 2000 | 0 | — | 67.1 |

Example 22

The same test as the one of Example 3 was effected using a Sumithion emulsion as an insecticide, and the enhancers 118 and 122 of Example 17 as enhancers each in the amount as specified in Table 26. The results are given in Table 26.

TABLE 26

| Test No. | Enhancer No. | Insecticide concn. (ppm) | Enhancer concn. (ppm) | Agricultural chemical concn./ enhancer concn. by wt. | Insecticidal-ratio (%) |
|---|---|---|---|---|---|
| 1 | 118 | 250 | 10 | 1/0.08 | 90.0 |
| 2 | | 250 | 25 | 1/0.2 | 93.3 |
| 3 | | 250 | 250 | 1/2 | 93.3 |
| 4 | | 250 | 1000 | 1/8 | 100 |
| 5 | | 250 | 2500 | 1/20 | 100 |
| 6 | | 250 | 5000 | 1/40 | 96.7 |
| 7 | 122 | 250 | 10 | 1/0.08 | 90.0 |
| 8 | | 250 | 25 | 1/0.2 | 90.0 |
| 9 | | 250 | 250 | 1/2 | 96.7 |
| 10 | | 250 | 1000 | 1/8 | 100 |
| 11 | | 250 | 2500 | 1/20 | 93.3 |
| 12 | | 250 | 5000 | 1/40 | 93.3 |
| 13 | — | 250 | 0 | — | 46.7 |

Example 31

By using compounds listed in Tables 31 and 32, enhancers for agricultural chemicals listed in Tables 33 to 35 were prepared.

The above-mentioned enhancers were each dissolved in deionized water to give a 0.2% by weight [as a content of an active ingredient(s)] dilution. With the use of the 0.2% by weight dilution thus obtained, commercially available herbicides, i.e., a Roundup liquid formulation (containing 41% by weight of isopropylamine salt of Glyphosate as an active ingredient), a Karmex wettable powder (containing 78.5% by weight of DCMU as an active ingredient) and Herblace water-soluble powder (containing 20% by weight of Bialaphos as an active ingredient) were each diluted 300-fold. Thus three agricultural chemical compositions were obtained for each enhancer for agricultural chemicals.

The same test as the one effected in Example 1 was carried out by using the agricultural chemical compositions thus prepared, and the herbicidal percentages were calculated in the same manner as that described in Example 1.

Tables 36 to 38 show the herbicidal percentages of the agricultural chemical compositions.

TABLE 31

| Compd. No. | Structure |
|---|---|
| 31 | $CH_3\underset{CH_3}{\overset{CH_2CH_2-COO-C_{10}H_{21}}{\diagdown\overset{\oplus}{N}\diagup}}\underset{C_{10}H_{21}}{\diagup\diagdown} \cdot Cl^-$ |
| 32 | $CH_3\underset{CH_3}{\overset{CH_3}{\diagdown\overset{\oplus}{N}\diagup}}\underset{CH_2CH_2-OCO-CH_2-(OCH_2CH_2)_5-OC_{12}H_{25}}{\diagup\diagdown} \cdot Cl^-$ |
| 33 | $HO-CH_2CH_2\underset{CH_3}{\overset{CH_2CH_2-COO-C_{16}H_{33}}{\diagdown\overset{\oplus}{N}\diagup}}\underset{CH_2CH_2CH_2-NHCO-C_{11}H_{23}}{\diagup\diagdown} \cdot CH_3SO_4^-$ |

TABLE 31-continued

| Compd. No. | Structure |
|---|---|
| 34 | $(CH_3)(C_2H_5)N^{\oplus}(CH_2-CONH-C_{18}H_{35})(C_{18}H_{35}) \cdot C_2H_5SO_4^-$ |
| 35 | $(CH_3)_2N^{\oplus}(CH_2-CONH-CH_2CH(C_2H_5)(CH_2)_3CH_3)(CH_2CH(C_2H_5)(CH_2)_3CH_3) \cdot Cl^-$ |
| 36 | $(CH_3)(H)N^{\oplus}(CH_2CH_2-COO-C_{18}H_{35})_2 \cdot Cl^-$ |
| 37 | $(CH_3)_2N^{\oplus}(C_{16}H_{33})(C_2H_4-OCO-CH_2-(OCH_2CH_2)_5-O-C_{16}H_{33}) \cdot Cl^-$ |
| 38 | $(CH_3)_2N^{\oplus}(CH_2-CO-(OCH_2CH_2)_{10}-O-C_8H_{17})_2 \cdot CH_3SO_4^-$ |
| 39 | $(CH_3)_2N^{\oplus}(C_2H_4-OCO-C_{11}H_{23})(C_3H_5-NHCO-CH_2-(OCH_2CH_2)_{10}-O-C_{16}H_{33}) \cdot Cl^-$ |
| 40 | $(CH_3)_2N^{\oplus}(C_2H_4-OCO-CH_2-(OCH_2CH_2)_5-O-C_{12}H_{25})(C_2H_5-NHCO-CH_2-(OCH_2CH_2)_5-O-C_{12}H_{25}) \cdot Cl^-$ |

TABLE 32

| Compd. No. | Structure |
|---|---|
| 41 | $(CH_3)_2N^{\oplus}(C_2H_4-NHCO-C_7H_{15})(CH_2-CO-(OCH_2CH_2)_{10}-O-C_{12}H_{25}) \cdot Cl^-$ |
| 42 | $(CH_3)(C_2H_5)N^{\oplus}(C_3H_6-NHCO-CH_2-(OCH_2CH_2)_{10}-O-C_8H_{17})_2 \cdot C_2H_5SO_4^-$ |
| 43 | $(C_4H_9)(CH_3)N^{\oplus}(C_{10}H_{21})(CH_2-CO-(OCH_2CH_2)_8-O-C_{12}H_{25}) \cdot Br^-$ |
| 44 | $(CH_3)_2N^{\oplus}(CH_2CH_2-OCO-CH_2-(OCH_2CH_2)_5-O-C_{12}H_{25})(CH_2-CO-(OCH_2CH_2)_5-O-C_{12}H_{25}) \cdot Cl^-$ |

TABLE 32-continued

| Compd. No. | Structure |
|---|---|
| 45 | CH₃—N⟨CH₂CH₂OCO—CH₂—(OCH₂CH₂)₁₀—O—C₁₀H₂₁ / C₃H₆—NHCO—CH₂—(OCH₂CH₂)₁₀—O—C₁₀H₂₁ |
| 46 | CH₃—N⟨CH₂CH₂—OCO—CH₂—(OCH₂CH₂)₅—O—C₁₂H₂₅ / CH₂CH₂—zoCO—CH₂—(OCH₂CH₂)₅—O—C₁₂H₂₅ |
| 47 | CH₃—N⟨C₃H₆NHCOCH₂(OCH₂CH₂)₉OC₁₈H₃₅ / C₃H₆NHCOCH₂(OCH₂CH₂)₉OC₁₈H₃₅ |
| 48 | HOCH₂CH₂—N⟨CH₂CO(OCH₂CH₂)₁₂OC₁₂H₂₅ / CH₂COOCH₂CH(CH₂)₃CH₃ with CH₂CH₃ branch |
| 49 | CH₃—N⟨CH₂CH₂OCOCH₂(OCH₂CH₂)₅OC₁₂H₂₅ / CH₂CO(OCH₂CH₂)₅OC₁₂H₂₅ |
| 50 | C₂H₅—N⟨C₁₂H₂₄—OH / CH₂CO(OCH₂CH₂)₁₀OC₁₅H₃₃ |

TABLE 33

| Enhancer No. | Compd. No. (A) | Surfactant (B) used together | (A)/(B) by wt. |
|---|---|---|---|
| 301 | (31) | — | 100/0 |
| 302 | (31) | POE(10) nonylphenyl ether | 80/20 |
| 303 | (31) | POE(6) sorbitan monooleate | 80/20 |
| 304 | (32) | — | 100/0 |
| 305 | (32) | POE(7) sec. C₁₂₋₁₃ ether | 80/20 |
| 306 | (32) | POE(20) sorbitan monolaurate | 80/20 |
| 307 | (33) | — | 100/0 |
| 308 | (33) | POE(9) nonylphenyl ether | 80/20 |
| 309 | (33) | POE(9) oleyl ether | 80/20 |
| 310 | (34) | — | 100/0 |
| 311 | (34) | POE(25) hardened castor oil | 80/20 |
| 312 | (34) | POE(9) octylphenyl ether | 80/20 |
| 313 | (35) | — | 100/0 |
| 314 | (35) | POE(20) sorbitan monooleate | 80/20 |
| 315 | (35) | POE(7) linear and branched C₁₂₋₁₃ ether | 80/20 |
| 316 | (36) | — | 100/0 |
| 317 | (36) | POE(10) nonylphenyl ether | 80/20 |
| 318 | (36) | POE(6) sorbitan monooleate | 80/20 |
| 319 | (37) | — | 100/0 |
| 320 | (37) | POE(9) nonylphenyl ether | 80/20 |
| 321 | (37) | POE(20) sorbitan monolaurate | 80/20 |

TABLE 34

| Enhancer No. | Compd. No. (A) | Surfactant (B) used together | (A)/(B) by wt. |
|---|---|---|---|
| 322 | (38) | — | 100/0 |
| 323 | (38) | POE(8) oleyl ether | 80/20 |
| 324 | (38) | POE(25) hardened castor oil | 80/20 |
| 325 | (39) | — | 100/0 |
| 326 | (39) | POE(25) hardened castor oil | 80/20 |
| 327 | (39) | POE(9) octylphenyl ether | 80/20 |
| 328 | (40) | — | 100/0 |
| 329 | (40) | POE(10) nonylphenyl ether | 80/20 |
| 330 | (40) | POE(7) linear and branched C₁₂₋₁₃ ether | 80/20 |
| 331 | (41) | — | 100/0 |
| 332 | (41) | POE(9) nonylphenyl ether | 80/20 |
| 333 | (41) | POE(20) sorbitan monolaurate | 80/20 |
| 334 | (42) | — | 100/0 |
| 335 | (42) | POE(10) nonylphenyl ether | 80/20 |
| 336 | (42) | POE(7) sec. C₁₂₋₁₃ ether | 80/20 |
| 337 | (43) | — | 100/0 |
| 338 | (43) | POE(10) nonylphenyl ether | 80/20 |
| 339 | (43) | POE(6) sorbitan monooleate | 80/20 |
| 340 | (44) | — | 100/0 |
| 341 | (44) | POE(6) lauryl ether | 80/20 |
| 342 | (44) | POE(20) sorbitan monolaurate | 80/20 |
| 343 | (45) | — | 100/0 |
| 344 | (45) | POE(10) nonylphenyl ether | 80/20 |
| 345 | (45) | POE(6) sorbitan monooleate | 80/20 |

TABLE 35

| Enhancer No. | Compd. No. (A) | Surfactant (B) used together | (A)/(B) by wt. |
|---|---|---|---|
| 346 | (46) | — | 100/0 |

TABLE 35-continued

| | | | |
|---|---|---|---|
| 347 | (46) | POE(9) nonylphenyl ether | 80/20 |
| 348 | (46) | POE(7) sec. $C_{12-13}$ ether | 80/20 |
| 349 | (47) | — | 100/0 |
| 350 | (47) | POE(10) nonylphenyl ether | 80/20 |
| 351 | (47) | POE(6) sorbitan monooleate | 80/20 |
| 352 | (48) | — | 100/0 |
| 353 | (48) | POE(6) lauryl ether | 80/20 |
| 354 | (48) | POE(20) sorbitan monolaurate | 80/20 |
| 355 | (49) | — | 100/0 |
| 356 | (49) | POE(10) nonylphenyl ether | 80/20 |
| 357 | (49) | POE(6) sorbitan monolaurate | 80/20 |
| 358 | (50) | — | 100/0 |
| 359 | (50) | POE(9) nonylphenyl ether | 80/20 |
| 360 | (50) | POE(7) sec. $C_{12-13}$ ether | 80/20 |
| 361 | dimethyldipalmitylammonium chloride | | — |
| 362 | trimethylcocoylammonium chloride | | — |
| 363 | POE(2) monomethylmonooctylammonium chloride | | — |
| 364 | POE(30) plamitylamine | | — |

Note:
Enhancer Nos. 361 to 364 are comparative ones.

TABLE 36

| | | Herbicidal percentage (%) | | |
|---|---|---|---|---|
| | Enhancer No. | Karmex wettable powder | Herbiace water-soluble powder | Roundup liquid formulation |
| Invention product | 301 | 89.3 | 97.4 | 98.1 |
| | 302 | 94.5 | 98.1 | 98.9 |
| | 303 | 93.2 | 98.0 | 97.6 |
| | 304 | 95.8 | 96.5 | 97.4 |
| | 305 | 97.6 | 95.8 | 96.5 |
| | 306 | 96.9 | 94.0 | 99.1 |
| | 307 | 98.1 | 97.6 | 97.3 |
| | 308 | 99.0 | 98.0 | 96.5 |
| | 309 | 99.0 | 98.0 | 95.7 |
| | 310 | 95.4 | 94.3 | 96.4 |
| | 311 | 97.2 | 96.2 | 98.8 |
| | 312 | 96.5 | 95.1 | 97.9 |
| | 313 | 96.1 | 98.8 | 98.1 |
| | 314 | 95.2 | 99.1 | 99.1 |
| | 315 | 96.1 | 99.1 | 99.7 |
| | 316 | 90.5 | 93.8 | 95.4 |
| | 317 | 93.2 | 95.6 | 97.2 |
| | 318 | 92.5 | 95.0 | 96.5 |
| | 319 | 89.8 | 97.5 | 98.1 |
| | 320 | 89.0 | 96.2 | 99.4 |
| | 321 | 91.5 | 96.9 | 98.9 |

TABLE 37

| | | Herbicidal percentage (%) | | |
|---|---|---|---|---|
| | Enhancer No. | Karmex wettable powder | Herbiace water-soluble powder | Roundup liquid formulation |
| Invention product | 322 | 95.2 | 98.2 | 96.2 |
| | 323 | 96.3 | 99.1 | 98.1 |
| | 324 | 95.0 | 99.3 | 98.1 |
| | 325 | 92.0 | 94.7 | 97.6 |
| | 326 | 90.4 | 96.2 | 98.3 |
| | 327 | 93.5 | 94.8 | 98.0 |
| | 328 | 94.1 | 95.9 | 99.8 |
| | 329 | 96.0 | 97.0 | 95.0 |
| | 330 | 97.2 | 97.0 | 97.4 |
| | 331 | 95.8 | 95.4 | 96.2 |
| | 332 | 96.2 | 95.0 | 96.2 |
| | 333 | 95.8 | 93.8 | 98.0 |
| | 334 | 92.1 | 98.0 | 97.2 |
| | 335 | 93.4 | 99.4 | 96.5 |

TABLE 37-continued

| | Herbicidal percentage (%) | | |
|---|---|---|---|
| Enhancer No. | Karmex wettable powder | Herbiace water-soluble powder | Roundup liquid formulation |
| 336 | 92.0 | 99.4 | 97.0 |
| 337 | 88.6 | 94.1 | 94.2 |
| 338 | 92.1 | 96.2 | 96.7 |
| 339 | 92.1 | 95.4 | 96.1 |
| 340 | 89.8 | 93.8 | 95.3 |
| 341 | 95.4 | 98.9 | 99.8 |
| 342 | 93.7 | 97.9 | 99.8 |

TABLE 38

| | | Herbicidal percentage (%) | | |
|---|---|---|---|---|
| | Enhancer No. | Karmex wettable powder | Herbiace water-soluble powder | Roundup liquid formulation |
| Invention product | 343 | 94.6 | 97.2 | 99.6 |
| | 344 | 90.2 | 94.1 | 97.4 |
| | 345 | 92.1 | 90.5 | 95.8 |
| | 346 | 95.6 | 96.3 | 98.9 |
| | 347 | 92.5 | 92.1 | 95.4 |
| | 348 | 93.3 | 91.8 | 96.2 |
| | 349 | 93.4 | 95.5 | 96.3 |
| | 350 | 92.3 | 97.3 | 96.8 |
| | 351 | 94.1 | 93.1 | 97.2 |
| | 352 | 88.5 | 91.5 | 95.2 |
| | 353 | 90.6 | 94.7 | 98.8 |
| | 354 | 92.8 | 95.8 | 99.2 |
| | 355 | 95.6 | 91.8 | 98.6 |
| | 356 | 94.1 | 93.4 | 99.1 |
| | 357 | 95.0 | 93.1 | 97.3 |
| | 358 | 89.9 | 96.1 | 95.4 |
| | 359 | 93.7 | 95.4 | 98.9 |
| | 360 | 92.1 | 90.2 | 96.7 |
| Comp. product | 361 | 56.5 | 72.5 | 73.8 |
| | 362 | 54.2 | 70.8 | 72.5 |
| | 363 | 65.1 | 74.2 | 77.6 |
| | 364 | 63.4 | 72.4 | 76.1 |
| no addition | | 42.1 | 63.9 | 65.7 |

Example 32

The same test as the one effected in Example 2 was carried out and the miticidal ratio was determined in the same manner as that described in Example 2, except that the enhancers for agricultural chemicals employed in Example 31 were used.

Tables 39 to 41 show the results.

TABLE 39

| | | Miticidal ratio (%) | |
|---|---|---|---|
| | Enhancer No. | Nissolan V emulsion | Osadan wettable powder-25 |
| Invention product | 301 | 97.8 | 98.9 |
| | 302 | 98.9 | 100 |
| | 303 | 98.9 | 100 |
| | 304 | 96.7 | 97.8 |
| | 305 | 97.8 | 98.9 |
| | 306 | 95.6 | 98.9 |
| | 307 | 100 | 100 |
| | 308 | 100 | 98.9 |
| | 309 | 98.9 | 98.9 |

TABLE 39-continued

|  | Miticidal ratio (%) | |
|---|---|---|
| Enhancer No. | Nissolan V emulsion | Osadan wettable powder-25 |
| 310 | 93.3 | 96.7 |
| 311 | 98.9 | 100 |
| 312 | 98.9 | 98.9 |
| 313 | 98.9 | 98.9 |
| 314 | 97.8 | 100 |
| 315 | 100 | 100 |
| 316 | 97.8 | 95.6 |
| 317 | 98.9 | 97.8 |
| 318 | 98.9 | 96.7 |
| 319 | 100 | 98.9 |
| 320 | 97.8 | 98.9 |
| 321 | 98.9 | 98.9 |

TABLE 40

|  |  | Miticidal ratio (%) | |
|---|---|---|---|
|  | Enhancer No. | Nissolan V emulsion | Osadan wettable powder-25 |
| Invention product | 322 | 94.4 | 92.2 |
|  | 323 | 96.7 | 97.8 |
|  | 324 | 95.6 | 93.3 |
|  | 325 | 98.9 | 98.9 |
|  | 326 | 100 | 100 |
|  | 327 | 100 | 100 |
|  | 328 | 93.3 | 96.7 |
|  | 329 | 97.8 | 98.9 |
|  | 330 | 95.6 | 97.8 |
|  | 331 | 97.8 | 100 |
|  | 332 | 100 | 100 |
|  | 333 | 98.9 | 98.9 |
|  | 334 | 94.4 | 92.2 |
|  | 335 | 98.9 | 95.6 |
|  | 336 | 97.8 | 93.3 |
|  | 337 | 96.7 | 94.4 |
|  | 338 | 97.8 | 95.6 |
|  | 339 | 97.8 | 94.4 |
|  | 340 | 98.9 | 98.9 |
|  | 341 | 94.4 | 95.6 |
|  | 342 | 97.8 | 95.6 |

TABLE 41

|  |  | Miticidal ratio (%) | |
|---|---|---|---|
|  | Enhancer No. | Nissolan V emulsion | Osadan wettable powder-25 |
| Invention product | 343 | 98.9 | 97.8 |
|  | 344 | 92.2 | 93.3 |
|  | 345 | 91.1 | 95.6 |
|  | 346 | 97.8 | 100 |
|  | 347 | 95.6 | 98.9 |
|  | 348 | 95.6 | 98.9 |
|  | 349 | 92.2 | 96.7 |
|  | 350 | 97.8 | 95.6 |
|  | 351 | 96.7 | 92.2 |
|  | 352 | 97.8 | 95.6 |
|  | 353 | 97.8 | 92.2 |
|  | 354 | 95.6 | 94.4 |
|  | 355 | 94.4 | 95.6 |
|  | 356 | 97.8 | 94.4 |
|  | 357 | 97.8 | 93.3 |
|  | 358 | 92.2 | 93.3 |
|  | 359 | 95.6 | 95.6 |
|  | 360 | 93.3 | 97.8 |
| Comp. product | 361 | 55.6 | 47.7 |
|  | 362 | 52.2 | 50.0 |
|  | 363 | 65.6 | 63.3 |
|  | 364 | 66.7 | 62.2 |

TABLE 41-continued

|  | Miticidal ratio (%) | |
|---|---|---|
| Enhancer No. | Nissolan V emulsion | Osadan wettable powder-25 |
| no addition | 47.7 | 42.2 |

Example 33

The same test as the one effected in Example 3 was carried out and the insecticidal ratio was determined in the same manner as that of Example 3, except that the enhancers for agricultural chemicals employed in Example 31 were used. Tables 42 to 44 show the results.

TABLE 42

|  |  | Insecticidal ratio (%) | |
|---|---|---|---|
|  | Enhancer No. | Sumithion emulsion | Malathon emulsion |
| Invention product | 301 | 96.7 | 96.7 |
|  | 302 | 96.7 | 96.7 |
|  | 303 | 100 | 100 |
|  | 304 | 96.7 | 93.3 |
|  | 305 | 93.3 | 96.7 |
|  | 306 | 100 | 100 |
|  | 307 | 93.3 | 96.7 |
|  | 308 | 96.7 | 96.7 |
|  | 309 | 94.4 | 93.3 |
|  | 310 | 96.7 | 96.7 |
|  | 311 | 100 | 100 |
|  | 312 | 100 | 100 |
|  | 313 | 93.3 | 96.7 |
|  | 314 | 96.7 | 93.3 |
|  | 315 | 93.3 | 96.7 |
|  | 316 | 93.3 | 96.7 |
|  | 317 | 96.7 | 96.7 |
|  | 318 | 96.7 | 96.7 |
|  | 319 | 90.0 | 86.7 |
|  | 320 | 96.7 | 93.3 |
|  | 321 | 96.7 | 93.3 |

TABLE 43

|  |  | Insecticidal ratio (%) | |
|---|---|---|---|
|  | Enhancer No. | Sumithion emulsion | Malathon emulsion |
| Invention product | 322 | 96.7 | 96.7 |
|  | 323 | 100 | 100 |
|  | 324 | 100 | 100 |
|  | 325 | 96.7 | 93.3 |
|  | 326 | 100 | 96.7 |
|  | 327 | 100 | 100 |
|  | 328 | 93.3 | 93.3 |
|  | 329 | 96.7 | 96.7 |
|  | 330 | 96.7 | 93.3 |
|  | 331 | 96.7 | 96.7 |
|  | 332 | 100 | 96.7 |
|  | 333 | 96.7 | 93.3 |
|  | 334 | 93.3 | 93.3 |
|  | 335 | 90.0 | 93.3 |
|  | 336 | 96.7 | 96.7 |
|  | 337 | 90.0 | 86.7 |
|  | 338 | 93.3 | 90.0 |
|  | 339 | 93.3 | 93.3 |
|  | 340 | 93.3 | 96.7 |
|  | 341 | 100 | 100 |
|  | 342 | 100 | 100 |

TABLE 44

| | Enhancer No. | Insecticidal ratio (%) | |
| --- | --- | --- | --- |
| | | Sumithion emulsion | Malathon emulsion |
| Invention product | 343 | 100 | 100 |
| | 344 | 96.7 | 93.3 |
| | 345 | 90.0 | 93.3 |
| | 346 | 100 | 100 |
| | 347 | 90.0 | 96.7 |
| | 348 | 93.3 | 93.3 |
| | 349 | 96.7 | 100 |
| | 350 | 96.7 | 96.7 |
| | 351 | 90.0 | 93.3 |
| | 352 | 90.0 | 93.3 |
| | 353 | 93.3 | 96.7 |
| | 354 | 90.0 | 90.0 |
| | 355 | 100 | 86.7 |
| | 356 | 96.7 | 93.3 |
| | 357 | 96.7 | 96.7 |
| | 358 | 96.7 | 100 |
| | 359 | 100 | 90.0 |
| | 360 | 93.3 | 93.3 |
| Comp. product | 361 | 46.7 | 53.3 |
| | 362 | 46.7 | 56.7 |
| | 363 | 60.0 | 56.7 |
| | 364 | 63.3 | 66.7 |
| no addition | | 43.3 | 50.0 |

Example 34

The same test as the one effected in Example 4 was carried out and the preventive value was determined in the same manner as that described in Example 4, except that the enhancers for agricultural chemicals employed in Example 31 were used. Tables 45 to 47 show the results.

TABLE 45

| | Enhancer No. | Preventive value Benlate wettable powder |
| --- | --- | --- |
| Invention present | 301 | 94 |
| | 302 | 98 |
| | 303 | 98 |
| | 304 | 97 |
| | 305 | 100 |
| | 306 | 100 |
| | 307 | 93 |
| | 308 | 95 |
| | 309 | 93 |
| | 310 | 92 |
| | 311 | 99 |
| | 312 | 99 |
| | 313 | 98 |
| | 314 | 100 |
| | 315 | 99 |
| | 316 | 96 |
| | 317 | 98 |
| | 318 | 98 |
| | 319 | 89 |
| | 320 | 93 |
| | 321 | 92 |

TABLE 46

| | Enhancer No. | Preventive value Benlate wettable powder |
| --- | --- | --- |
| Invention present | 322 | 92 |
| | 323 | 95 |
| | 324 | 94 |
| | 325 | 99 |
| | 326 | 100 |

TABLE 46-continued

| | Enhancer No. | Preventive value Benlate wettable powder |
| --- | --- | --- |
| | 327 | 98 |
| | 328 | 92 |
| | 329 | 92 |
| | 330 | 96 |
| | 331 | 94 |
| | 332 | 98 |
| | 333 | 98 |
| | 334 | 93 |
| | 335 | 98 |
| | 336 | 99 |
| | 337 | 88 |
| | 338 | 90 |
| | 339 | 94 |
| | 340 | 92 |
| | 341 | 96 |
| | 342 | 94 |

TABLE 47

| | Enhancer No. | Preventive value Benlate wettable powder |
| --- | --- | --- |
| Invention present | 343 | 100 |
| | 344 | 96 |
| | 345 | 90 |
| | 346 | 94 |
| | 347 | 89 |
| | 348 | 90 |
| | 349 | 98 |
| | 350 | 96 |
| | 351 | 88 |
| | 352 | 90 |
| | 353 | 94 |
| | 354 | 96 |
| | 355 | 96 |
| | 356 | 90 |
| | 357 | 92 |
| | 358 | 96 |
| | 359 | 100 |
| | 360 | 92 |
| Comp. product | 361 | 65 |
| | 362 | 67 |
| | 363 | 72 |
| | 364 | 76 |
| no addition | | 61 |

The above Examples 31 to 34 show tests whereby the efficacies of the enhancers for agricultural chemicals of the present invention were compared with those of common cationic surfactants (comparative products) employed as enhancers for agricultural chemicals. As Tables 36 to 47 clearly indicate, the enhancers for agricultural chemicals of the present invention exerted remarkable effects and thus were usable on a practical level. In contrast, the comparative products somewhat enhanced the efficacies of the agricultural chemicals but were not effective on a practical level. Accordingly, it is observed that the enhancers for agricultural chemicals of the present invention would specifically enhance the efficacies of agricultural chemicals as compared with common cationic surfactants.

Example 35

The same test as the one effected in Example 1 was carried out by using a Roundup liquid formulation (containing 41% by weight of active ingredient) as a herbicide, and the enhancers 301, 306, 315, 319, 323 and 343 of Example 31 as enhancers each in the amount as specified in Tables 48 and 49. The results are given in Tables 48 and 49.

TABLE 48

| Test No. | Enhancer No. | Herbicide concn. (ppm) | Enhancer concn. (ppm) | Agricultural chemical concn./enhancer concn. by wt. | Herbicidal percentage (%) |
|---|---|---|---|---|---|
| 1 | 301 | 2000 | 0 | 1/0.06 | 87.9 |
| 2 | | 2000 | 100 | 1/0.12 | 91.3 |
| 3 | | 2000 | 500 | 1/0.6 | 95.0 |
| 4 | | 2000 | 1000 | 1/1.2 | 99.1 |
| 5 | | 2000 | 5000 | 1/6 | 99.7 |
| 6 | | 2000 | 10000 | 1/12 | 98.8 |
| 7 | | 2000 | 30000 | 1/37 | 98.1 |
| 8 | 306 | 2000 | 50 | 1/0.06 | 88.1 |
| 9 | | 2000 | 100 | 1/0.12 | 90.3 |
| 10 | | 2000 | 500 | 1/0.6 | 94.8 |
| 11 | | 2000 | 1000 | 1/1.2 | 97.3 |
| 12 | | 2000 | 5000 | 1/6 | 99.2 |
| 13 | | 2000 | 10000 | 1/12 | 97.4 |
| 14 | | 2000 | 30000 | 1/37 | 96.5 |
| 15 | 315 | 2000 | 50 | 1/0.06 | 87.6 |
| 16 | | 2000 | 100 | 1/0.12 | 92.5 |
| 17 | | 2000 | 500 | 1/0.6 | 95.2 |
| 18 | | 2000 | 1000 | 1/1.2 | 98.0 |
| 19 | | 2000 | 5000 | 1/6 | 98.9 |
| 20 | | 2000 | 10000 | 1/12 | 98.0 |
| 21 | | 2000 | 30000 | 1/37 | 97.2 |

TABLE 49

| Test No. | Enhancer No. | Herbicide concn. (ppm) | Enhancer concn. (ppm) | Agricultural chemical concn./enhancer concn. by wt. | Herbicidal percentage (%) |
|---|---|---|---|---|---|
| 22 | 319 | 2000 | 50 | 1/0.06 | 85.1 |
| 23 | | 2000 | 100 | 1/0.12 | 89.3 |
| 24 | | 2000 | 500 | 1/0.6 | 92.1 |
| 25 | | 2000 | 1000 | 1/1.2 | 98.5 |
| 26 | | 2000 | 5000 | 1/6 | 99.5 |
| 27 | | 2000 | 10000 | 1/12 | 99.0 |
| 28 | | 2000 | 30000 | 1/37 | 98.1 |
| 29 | 323 | 2000 | 50 | 1/0.06 | 88.2 |
| 30 | | 2000 | 100 | 1/0.12 | 90.0 |
| 31 | | 2000 | 500 | 1/0.6 | 93.4 |
| 32 | | 2000 | 1000 | 1/1.2 | 97.2 |
| 33 | | 2000 | 5000 | 1/6 | 99.7 |
| 34 | | 2000 | 10000 | 1/12 | 97.5 |
| 35 | | 2000 | 30000 | 1/37 | 95.8 |
| 36 | 343 | 2000 | 50 | 1/0.06 | 84.9 |
| 37 | | 2000 | 100 | 1/0.12 | 88.5 |
| 38 | | 2000 | 500 | 1/0.6 | 93.0 |
| 39 | | 2000 | 1000 | 1/1.2 | 98.0 |
| 40 | | 2000 | 5000 | 1/6 | 99.8 |
| 41 | | 2000 | 10000 | 1/12 | 97.2 |
| 42 | | 2000 | 30000 | 1/37 | 97.0 |
| 43 | — | 2000 | 0 | — | 71.3 |

Example 36

The same test as the one effected in Example 3 was carried out by using a Sumithion emulsion as an insecticide, and the enhancers 304, 311, 322 and 327 of Example 31 as enhancers each in the amount as specified in Tables 50 and 51. The results are given in Tables 50 and 51.

TABLE 50

| Test No. | Enhancer No. | Insecticide concn. (ppm) | Enhancer concn. (ppm) | Agricultural chemical concn./enhancer concn. by wt. | Insecticidal ratio (%) |
|---|---|---|---|---|---|
| 1 | 304 | 250 | 10 | 1/0.08 | 86.7 |
| 2 | | 250 | 25 | 1/0.2 | 90.0 |
| 3 | | 250 | 250 | 1/2 | 93.3 |
| 4 | | 250 | 1000 | 1/8 | 96.7 |
| 5 | | 250 | 2500 | 1/20 | 96.7 |
| 6 | | 250 | 5000 | 1/40 | 93.3 |
| 7 | 311 | 250 | 10 | 1/0.08 | 83.3 |
| 8 | | 250 | 25 | 1/0.2 | 90.0 |
| 9 | | 250 | 250 | 1/2 | 96.7 |
| 10 | | 250 | 1000 | 1/8 | 100 |
| 11 | | 250 | 2500 | 1/20 | 100 |
| 12 | | 250 | 5000 | 1/40 | 96.7 |

TABLE 51

| Test No. | Enhancer No. | Insecticide concn. (ppm) | Enhancer concn. (ppm) | Agricultural chemical concn./enhancer concn. by wt. | Insecticidal ratio (%) |
|---|---|---|---|---|---|
| 13 | 322 | 250 | 10 | 1/0.08 | 86.7 |
| 14 | | 230 | 25 | 1/0.2 | 90.0 |
| 15 | | 250 | 250 | 1/2 | 93.3 |
| 16 | | 250 | 1000 | 1/8 | 96.7 |
| 17 | | 250 | 2500 | 1/20 | 96.7 |
| 18 | | 250 | 5000 | 1/40 | 93.3 |
| 19 | 327 | 250 | 10 | 1/0.08 | 86.7 |
| 20 | | 250 | 25 | 1/0.2 | 93.3 |
| 21 | | 230 | 250 | 1/2 | 96.7 |
| 22 | | 250 | 1000 | 1/8 | 100 |
| 23 | | 250 | 2500 | 1/20 | 100 |
| 24 | | 250 | 5000 | 1/40 | 96.7 |
| 25 | — | 250 | 0 | — | 43.3 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. An agricultural chemical composition comprising an agricultural chemical and an effective amount for enhancing the effectiveness of the agricultural chemical of an enhancer compound selected from the group consisting of compounds represented by the following formulae (A) to (F):

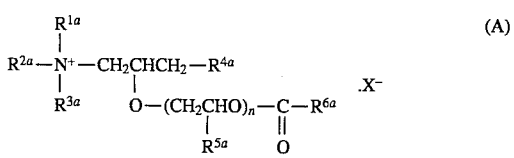

(A)

wherein $R^{1a}$ and $R^{2a}$ may be the same or different from each other and each represents an alkyl group having 1 to 4 carbon atoms, a group represented by the formula:

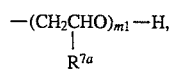

wherein each of $R^{7a}$s represents a hydrogen atom or a methyl group, and m1 is from 1 to 30, or a group represented by the formula:

$$-(CH_2CHO)_{m2}-\underset{R^{14a}}{\overset{\overset{\displaystyle O}{\|}}{C}}-R^{13a},$$

wherein $R^{13a}$ represents a linear or branched alkyl or alkenyl group having 5 to 36 carbon atoms which may be substituted by a hydroxyl group, each of $R^{14a}$s represents a hydrogen atom or a methyl group, and m2 is from 1 to 30;

$R^{3a}$ represents a hydrogen atom, a benzyl group or an alkyl group having 1 to 4 carbon atoms;

$R^{4a}$ represents a group represented by the formula:

$$-O-(CH_2CHO)_{q1}-\underset{R^{8a}}{\overset{\overset{\displaystyle O}{\|}}{C}}-R^{9a},$$

wherein each of $R^{8a}$s represents a hydrogen atom or a methyl group, $R^{9a}$ represents a linear or branched alkyl or alkenyl group having 5 to 36 carbon atoms which may be substituted with a hydroxyl group, and q1 is from 0 to 30, a group represented by the formula: —NHCOR$^{10a}$, wherein R$^{10a}$ represents a linear or branched alkyl or alkenyl group having 5 to 36 carbon atoms which may be substituted with a hydroxyl group, or a group represented by the formula:

$$-O-(CHCH_2O)_{q2}-R^{12a},$$
$$\phantom{-O-(}R^{11a}$$

wherein each of $R^{11a}$s represents a hydrogen atom or a methyl group, $R^{12a}$ represents a linear or branched alkyl or alkenyl group having 5 to 36 carbon atoms which may be substituted with a hydroxyl group, and q2 is from 0 to 30;

each of $R^{5a}$s represents a hydrogen atom or a methyl group;

$R^{6a}$ represents a linear or branched alkyl or alkenyl group having 5 to 35 carbon atoms which may be substituted with a hydroxyl group;

n is from 0 to 30; and

X⁻ represents a counter ion, $$\begin{array}{c}R^{1b}\\ \diagdown\\ \phantom{R}\\ \diagup\\ R^{2b}\end{array}NCH_2CHCH_2O\underset{\|}{\overset{O}{C}}_uH_{2u}(OCHCH_2)_wOR^{3b}\quad (B)$$
$$\phantom{R^{2b}\diagup}OC_tH_{2t}(OCHCH_2)_vOR^{4b}$$
$$\phantom{R^{2b}\diagup O}\|\phantom{C_tH_{2t}(OCHCH_2)_v}|$$
$$\phantom{R^{2b}\diagup}O\phantom{C_tH_{2t}(OCHCH_2)_v}R^{6b}$$

wherein $R^{1b}$ and $R^{2b}$ may be the same or different from each other and each represents an alkyl group having 1 to 4 carbon atoms which may be substituted with a hydroxyl group;

$R^{3b}$ and $R^{4b}$ may be the same or different from each other and each represents a linear or branched alkyl or alkenyl group having 4 to 36 carbon atoms which may be substituted with a hydroxyl group;

each of $R^{5b}$s and $R^{6b}$s represents a hydrogen atom or a methyl group;

t and u may be the same or different from each other and each represents a positive number of from 1 to 5; and v and w may be the same or different from each other and each represents a number of from 0 to $$\begin{array}{c}R^{7c}\\ \diagdown\\ \phantom{R}\\ \diagup\\ R^{9c}\end{array}N^+CH_2CHCH_2O\underset{\|}{\overset{O}{C}}_jH_{2j}(OCHCH_2)_rOR^{10c}\quad X^-\quad (C)$$
$$\phantom{R^{9c}\diagup}OC_kH_{2k}(OCHCH_2)_sOR^{11c}$$
$$\phantom{R^{9c}\diagup O}\|\phantom{C_kH_{2k}(OCHCH_2)_s}|$$
$$\phantom{R^{9c}\diagup}O\phantom{C_kH_{2k}(OCHCH_2)_s}R^{13c}$$

wherein $R^{7c}$ and $R^{8c}$ may be the same or different from each other and each represents an alkyl group having 1 to 4 carbon atoms;

$R^{9c}$ represents a hydrogen atom, a benzyl group or an alkyl group having 1 to 4 carbon atoms;

$R^{10c}$ and $R^{11c}$ may be the same or different from each other and each represents a linear or branched alkyl or alkenyl group having 4 to 36 carbon atoms which may be substituted with a hydroxyl group;

each of $R^{12c}$s and $R^{13c}$s represents a hydrogen atom or a methyl group;

j and k may be the same or different from each other and each represents a positive number of from 1 to 5;

r and s may be the same or different from each other and each represents a number of from 0 to 30; and X⁻ represents a counter ion, $$R^{1d}-N\diagup^{R^{2d}}_{\diagdown R^{3d}}\quad (D)$$

wherein $R^{1d}$ represents an alkyl group having 1 to 4 carbon atoms which may be substituted with a hydroxyl group;

$R^{2d}$ represents a linear or branched alkyl or alkenyl group having 1 to 36 carbon atoms which may be substituted with a hydroxyl group, a group represented by the formula: —$C_aH_{2a}$—(G$^1$)—R$^{4d}$, wherein R$^{4d}$ represents a linear or branched alkyl or alkenyl group having 5 to 36 carbon atoms which may be substituted with a hydroxyl group, G$^1$ represents a group represented by the formula: —OCO— or a group represented by the formula: —NHCO—, and a represents a positive number of 2 to 6, a group represented by the formula:

$$-C_bH_{2b}-\underset{\|}{\overset{O}{C}}-\underset{R^{6d}}{\overset{|}{\phantom{C}}}(OCHCH_2)_cOR^{5d},$$

wherein $R^{5d}$ represents a linear or branched alkyl or alkenyl group having 6 to 36 carbon atoms which may be substituted with a hydroxyl group, each of $R^{6d}$s represents a hydrogen atom or a methyl group, b represents a positive number of 1 to 5, and c represents a number of 0 to 30 or a group represented by the formula:

$$-C_eH_{2e}-(G^2)-C_fH_{2f}-\underset{R^{8d}}{\overset{|}{\phantom{C}}}(OCHCH_2)_gOR^{7d},$$

wherein $R^{7d}$ represents a linear or branched alkyl or alkenyl group having 4 to 36 carbon atoms which may be substituted with a hydroxyl group, each of R8ds represents a hydrogen atom or a methyl group, G$^2$ represents a group represented by the formula: —OCO— or a group represented by the formula: —NHCO—, e represents a positive number of 2 to 6, f represents a positive number of 1 to 5 and g represents a number of 0 to 30; and $R^{3d}$ represents a group represented by the formula:

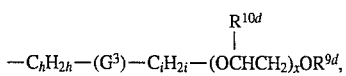
$$-C_hH_{2h}-(G^3)-C_iH_{2i}-(OCHCH_2)_xOR^{9d},$$

wherein $R^{9d}$ represents a linear or branched alkyl or alkenyl group having 4 to 36 carbon atoms which may be substituted with a hydroxyl group, each of $R^{10d}$s represents a hydrogen atom or a methyl group, $G^3$ represents a group represented by the formula: —OCO— or a group represented by the formula: —NHCO—, h represents a positive number of 2 to 6, i represents a positive number of 1 to 5, and x represents a number of 0 to 30 or a group represented by the formula:

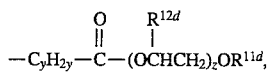
$$-C_yH_{2y}-\overset{O}{\overset{\|}{C}}-(OCHCH_2)_zOR^{11d},$$

wherein $R^{11d}$ represents a linear or branched alkyl or alkenyl group having 6 to 36 carbon atoms which may be substituted with a hydroxyl group, each of $R^{12d}$s represents a hydrogen atom or a methyl group, y represents a positive number of 1 to 5, and z represents a number of 0 to 30,

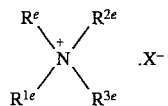
(E)

wherein $R^e$ represents a hydrogen atom, a benzyl group or an alkyl group having 1 to 4 carbon atoms which may be substituted with a hydroxyl group;

$R^{1e}$ represents an alkyl group having 1 to 4 carbon atoms which may be substituted with a hydroxyl group;

$R^{2e}$ represents a linear or branched alkyl or alkenyl group having 5 to 36 carbon atoms which may be substituted with a hydroxyl group, a group represented by the formula: $-C_aH_{2a}-(G^1)-R^{4e}$, wherein $R^{4e}$ represents a linear or branched alkyl or alkenyl group having 5 to 36 carbon atoms which may be substituted with a hydroxyl group, $G^1$ represents a group represented by the formula: —OCO— or a group represented by the formula: —NHCO—, and a represents a positive number of 2 to 6, a group represented by the formula:

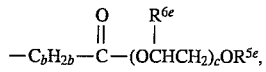
$$-C_bH_{2b}-\overset{O}{\overset{\|}{C}}-(OCHCH_2)_cOR^{5e},$$

wherein $R^{5e}$ represents a linear or branched alkyl or alkenyl group having 6 to 36 carbon atoms which may be substituted with a hydroxyl group, each of $R^{6e}$s represents a hydrogen atom or a methyl group, b represents a positive number of 1 to 5, and c represents a number of 0 to 30, or a group represented by the formula:

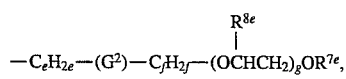
$$-C_eH_{2e}-(G^2)-C_fH_{2f}-(OCHCH_2)_gOR^{7e},$$

wherein $R^{7e}$ represents a linear or branched alkyl or alkenyl group having 4 to 36 carbon atoms which may be substituted with a hydroxyl group, each of $R^{8e}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of 0 to 30;

$R^{3e}$ represents a group represented by the formula:

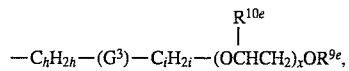
$$-C_hH_{2h}-(G^3)-C_iH_{2i}-(OCHCH_2)_xOR^{9e},$$

wherein $R^{9e}$ represents a linear or branched alkyl or alkenyl group having 4 to 36 carbon atoms which may be substituted with a hydroxyl group, each of $R^{10e}$s represents a hydrogen atom or a methyl group, $G^3$ represents a group represented by the formula: —OCO— or a group represented by the formula: —NHO—, h represents a positive number of 2 to 6, i represents a positive number of 1 to 5, and x represents a number of 0 to 30, or a group represented by the formula:

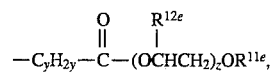
$$-C_yH_{2y}-\overset{O}{\overset{\|}{C}}-(OCHCH_2)_zOR^{11e},$$

wherein $R^{11e}$ represents a linear or branched alkyl or alkenyl group having 6 to 36 carbon atoms which may be substituted with a hydroxyl group, each of $R^{12e}$s represents a hydrogen atom or a methyl group, y represents a positive number of 1 to 5, and z represents a number of 0 to 30; and $X^-$ represents a counter ion, and

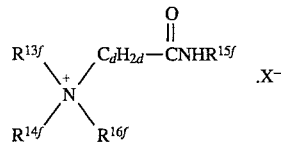
(F)

wherein $R^{13f}$ represents a hydrogen atom, a benzyl group or an alkyl group having 1 to 4 carbon atoms which may be substituted with a hydroxyl group;

$R^{14f}$ represents an alkyl group having 1 to 4 carbon atoms which may be substituted with a hydroxyl group;

$R^{15f}$ represents a linear or branched alkyl or alkenyl group having 5 to 36 carbon atoms which may be substituted with a hydroxyl group;

$R^{16f}$ represents a linear or branched alkyl or alkenyl group having 5 to 36 carbon atoms which may be substituted with a hydroxyl group;

d is a positive number of 1 to 5; and $X^-$ is a counter ion.

2. The agricultural chemical composition as claimed in claim 1, wherein the enhancer compound is selected from the group consisting of compounds represented by the above formula (A).

3. The agricultural chemical composition as claimed in claim 1, wherein the enhancer compound is selected from the group consisting of compounds represented by the above formulae (B) or (C).

4. The agricultural chemical composition as claimed in claim 1, wherein the enhancer compound is selected from The group consisting of compounds represented by the above formulae (D), (E) or (F).

5. The agricultural chemical composition as claimed in claim 1, wherein the weight ratio of the compound(s) represented by the above formulae (A) to (F) to the agricultural chemical(s) is from 0.05 to 50.

6. The agricultural chemical composition as claimed in claim 1, wherein the weight ratio of the compound(s) represented by the above general formulae (A) to (F) to the agricultural chemical(s) is from 0.1 to 10.

7. The agricultural chemical composition as claimed in claim 1, wherein the agricultural chemical is a fungicide, an insecticide, a miticide, a herbicide or a plant growth regulator.

8. The agricultural chemical composition as claimed in claim 1, which further comprises a surfactant other than the compounds represented by the formulae (A) to (F).

9. The agricultural chemical composition as claimed in claim 8, wherein the surfactant is a nonionic surfactant.

10. The agricultural chemical composition as claimed in claim 1, wherein the weight ratio of the compound(s) represented by the above formulae (A) to (F) to the surfactant(s) other than the compounds represented by the above formulae (A) to (F) is from 1/10 to 50/1.

11. The agricultural chemical composition as claimed in claim 1, wherein $R^{3a}$ in formula (A) represents a hydrogen atom or an alkyl group having 1 to 4 carbon atoms; $R^{1b}$ and $R^{2b}$ in formula (B) may be the same or different from each other and each represents an alkyl group having 1 to 4 carbon atoms; $R^{9c}$ in formula (C) represents a hydrogen atom or an alkyl group having 1 to 4 carbon atoms; $R^{2d}$ in formula (D) represents a linear or branched alkyl or alkenyl group having 5 to 36 carbon atoms which may be substituted with a hydroxyl group, a group represented by the formula: $-C_aH_{2a}-(G^1)-R^{4d}$, wherein $R^{4d}$ represents a linear or branched alkyl or alkenyl group having 5 to 36 carbon atoms which may be substituted with a hydroxyl group, $G^1$ represents a group represented by the formula: —OCO— or a group represented by the formula: —NHCO—, and a represents a positive number of 2 to 6, a group represented by the formula:

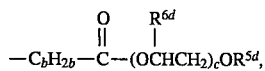

wherein $R^{5d}$ represents a linear or branched alkyl or alkenyl group having 6 to 36 carbon atoms which may be substituted with a hydroxyl group, each of $R^{6d}$s represents a hydrogen atom or a methyl group, b represents a positive number of 1 to 5, and c represents a number of 0 to 30, or a group represented by the formula:

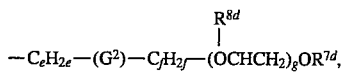

wherein $R^{7d}$ represents a linear or branched alkyl or alkenyl group having 4 to 36 carbon atoms which may be substituted with a hydroxyl group, each of $R^{8d}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of 0 to 30; $R^e$ in formula (E) represents a hydrogen atom or an alkyl group having 1 to 4 carbon atoms which may be substituted with a hydroxyl group; $R^{2e}$ in formula (E) represents a linear or branched alkyl or alkenyl group having 5 to 36 carbon atoms which may be substituted with a hydroxyl group, a group represented by the formula: $-C_aH_{2a}-(G^1)-R^{4e}$, wherein $R^{4e}$ represents a linear or branched alkyl or alkenyl group having 5 to 36 carbon atoms which may be substituted with a hydroxyl group, $G^1$ represents a group represented by the formula: —OCO— or a group represented by the formula: —NHCO—, and a represents a positive number of 2 to 6, a group represented by the formula:

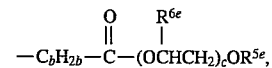

wherein $R^{5e}$ represents a linear or branched alkyl or alkenyl group having 6 to 36 carbon atoms which may be substituted with a hydroxyl group, each of $R^{6e}$s represents a hydrogen atom or a methyl group, b represents a positive number of 1 to 5, and c represents a number of 0 to 30 or a group represented by the formula:

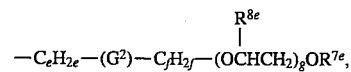

wherein $R^{7e}$ represents a linear or branched alkyl or alkenyl group having 4 to 36 carbon atoms which may be substituted with a hydroxyl group, each of $R^{8e}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of to 30; $R^{13f}$ in formula (F) represents a hydrogen atom or an alkyl group having 1 to 4 carbon atoms which may be substituted with a hydroxyl group.

12. The agricultural chemical composition as claimed in claim 11, wherein the enhancer compound is selected from the group consisting of compounds represented by the above formula (A).

13. The agricultural chemical composition as claimed in claim 11, wherein the enhancer compound is selected from the group consisting of compounds represented by the above formulae (B) or (C).

14. The agricultural chemical composition as claimed in claim 11, wherein the enhancer compound is selected from the group consisting of compounds represented by the above formulae (D), (E) or (F).

15. The agricultural chemical composition as claimed in claim 1, wherein said enhancer compound is

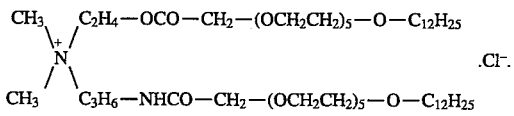

16. The agricultural chemical composition as claimed in claim 1, wherein said enhancer compound is

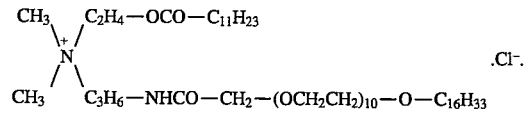

17. The agricultural chemical composition as claimed in claim 1, wherein said enhancer compound is

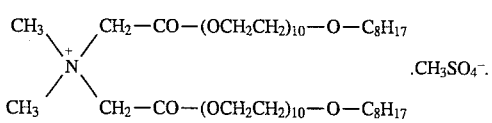

18. The agricultural chemical composition as claimed in claim 1, wherein said enhancer compound is

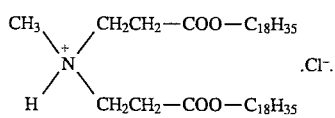

19. The agricultural chemical composition as claimed in claim 1, wherein said enhancer compound is

20. The agricultural chemical composition as claimed in claim 1, wherein said enhancer compound is

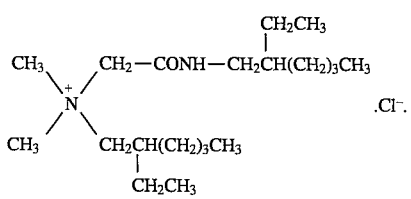

21. The agricultural chemical composition as claimed in claim 1, wherein said enhancer compound is

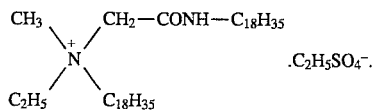

22. The agricultural chemical composition as claimed in claim 1, wherein said enhancer compound is

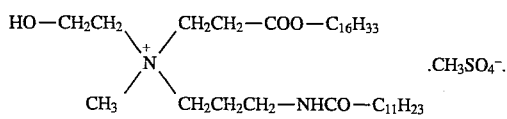

23. The agricultural chemical composition as claimed in claim 1, wherein said enhancer compound is

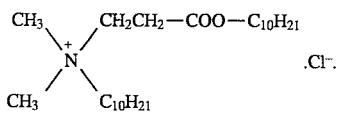

24. The agricultural chemical composition as claimed in claim 1, wherein said enhancer compound is

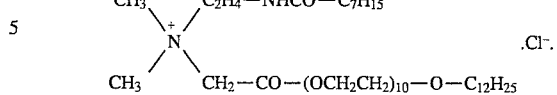

25. The agricultural chemical composition as claimed in claim 1, wherein said enhancer compound is

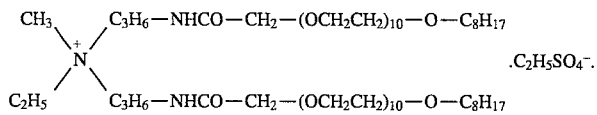

26. The agricultural chemical composition as claimed in claim 1, wherein said enhancer compound is

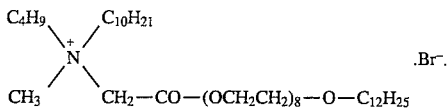

27. The agricultural chemical composition as claimed in claim 1, wherein said enhancer compound is

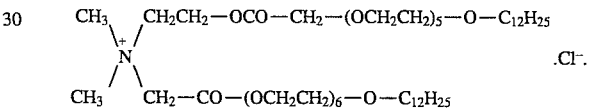

28. An agricultural chemical composition comprising an agricultural chemical and an effective amount for enhancing the effectiveness of the agricultural chemical of an enhancer compound of the following formula:

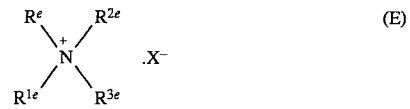

wherein $R^e$ represents a hydrogen atom, a benzyl group or an alkyl group having 1 to 4 carbon atoms which may be substituted with a hydroxyl group;

$R^{1e}$ represents an alkyl group having 1 to 4 carbon atoms which may be substituted with a hydroxyl group;

$R^{2e}$ represents a linear or branched alkyl or alkenyl group having 5 to 36 carbon atoms which may be substituted with a hydroxyl group, a group represented by the formula: $-C_aH_{2a}-(G^1)-R^{4e}$, wherein $R^{4e}$ represents a linear or branched alkyl or alkenyl group having 5 to 36 carbon atoms which may be substituted with a hydroxyl group, $G^1$ represents a group represented by the formula: $-OCO-$ or a group represented by the formula: $-NHCO-$, and a represents a positive number of 2 to 6, a group represented by the formula:

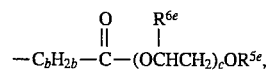

wherein $R^{5e}$ represents a linear or branched alkyl or alkenyl group having 6 to 36 carbon atoms which may be substituted with a hydroxyl group, each of $R^{6e}$s represents a hydrogen atom or a methyl group, b represents a positive number of 1 to 5, and c represents a number of 0 to 30, or a group represented by the formula:

$$-C_eH_{2e}-(G^2)-C_fH_{2f}-(OCHCH_2)_gOR^{7e},$$
$$\qquad\qquad\qquad\qquad\qquad\quad |$$
$$\qquad\qquad\qquad\qquad\qquad R^{8e}$$

wherein $R^{7e}$ represents a linear or branched alkyl or alkenyl group having 4 to 36 carbon atoms which may be substituted with a hydroxyl group, each of $R^{8e}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of 0 to 30;

$R^{3e}$ represents a group represented by the formula:

$$-C_hH_{2h}-(G^3)-C_iH_{2i}-(OCHCH_2)_xOR^{9e},$$
$$\qquad\qquad\qquad\qquad\qquad\quad |$$
$$\qquad\qquad\qquad\qquad\qquad R^{10e}$$

wherein $R^{9e}$ represents a linear or branched alkyl or alkenyl group having 4 to 36 carbon atoms which may be substituted with a hydroxyl group, each of $R^{10e}$s represents a hydrogen atom or a methyl group, $G^3$ represents a group represented by the formula —OCO— or a group represented by the formula: —NHCO—, h represents a positive number of 2 to 6, i represents a positive number of 1 to 5, and x represents a number of 0 to 30, or a group represented by the formula:

$$\qquad\qquad O \quad\; R^{12e}$$
$$\qquad\qquad || \quad\;\; |$$
$$-C_yH_{2y}-C-(OCHCH_2)_zOR^{11e},$$

wherein $R^{11e}$ represents a linear or branched alkyl or alkenyl group having 6 to 36 carbon atoms which may be substituted with a hydroxyl group, each of $R^{12e}$s represents a hydrogen atom or a methyl group, y represents a positive number of 1 to 5, and z represents a number of 0 to 30; and $X^-$ represents a counter ion.

29. A method for enhancing the effectiveness of an agricultural chemical which comprises applying an enhancer compound selected from the group consisting of compounds represented by the following formulae (A) to (F) with an agricultural chemical to a locus which would benefit from such treatment:

$$\qquad\quad R^{1a} \qquad\qquad\qquad\qquad\qquad\qquad\quad (A)$$
$$\qquad\qquad |$$
$$R^{2a}-N^+-CH_2CHCH_2-R^{4a}$$
$$\qquad\quad |\qquad\qquad |\qquad\qquad\qquad\qquad\quad .X^-$$
$$\qquad R^{3a}\quad O-(CH_2CHO)_n-C-R^{6a}$$
$$\qquad\qquad\qquad\qquad\qquad |\quad\;\; ||$$
$$\qquad\qquad\qquad\qquad\qquad R^{5a}\;\; O$$

wherein $R^{1a}$ and $R^{2a}$ may be the same or different from each other and each represents an alkyl group having 1 to 4 carbon atoms, a group represented by the formula:

$$-(CH_2CHO)_{m1}-H,$$
$$\qquad\quad |$$
$$\qquad R^{7a}$$

wherein each of $R^{7a}$s represents a hydrogen atom or a methyl group, and m1 is from 1 to 30, or a group represented by the formula:

$$-(CH_2CHO)_{m2}-C-R^{13a},$$
$$\qquad\quad |\qquad\qquad ||$$
$$\qquad R^{14a}\qquad\; O$$

wherein $R^{13a}$ represents a linear or branched alkyl or alkenyl group having 5 to 36 carbon atoms which may be substituted by a hydroxyl group, each of $R^{14a}$s represents a hydrogen atom or a methyl group, and m2 is from 1 to 30;

$R^{3a}$ represents a hydrogen atom, a benzyl group or an alkyl group having 1 to 4 carbon atoms;

$R^{4a}$ represents a group represented by the formula:

$$-O-(CH_2CHO)_{q1}-C-R^{9a},$$
$$\qquad\qquad\quad |\qquad\qquad ||$$
$$\qquad\qquad R^{8a}\qquad\; O$$

wherein each of $R^{8a}$s represents a hydrogen atom or a methyl group, $R^{9a}$ represents a linear or branched alkyl or alkenyl group having 5 to 36 carbon atoms which may be substituted with a hydroxyl group, and q1 is from 0 to 30, a group represented by the formula: —NHCOR$^{10a}$, wherein $R^{10a}$ represents a linear or branched alkyl or alkenyl group having 5 to 36 carbon atoms which may be substituted with a hydroxyl group, or a group represented by the formula:

$$-O-(CHCH_2O)_{q2}-R^{12a},$$
$$\qquad\quad |$$
$$\qquad R^{11a}$$

wherein each of $R^{11a}$s represents a hydrogen atom or a methyl group, $R^{12a}$ represents a linear or branched alkyl or alkenyl group having 5 to 36 carbon atoms which may be substituted with a hydroxyl group, and q2 is from 0 to 30;

each of $R^{5a}$s represents a hydrogen atom or a methyl group;

$R^{6a}$ represents a linear or branched alkyl or alkenyl group having 5 to 35 carbon atoms which may be substituted with a hydroxyl group;

n is from 0 to 30; and $X^-$ represents a counter ion, $$R^{1b}\qquad\qquad\quad O \quad\; R^{5b} \qquad\qquad\qquad (B)$$
$$\quad\;\backslash \qquad\qquad\quad || \quad\;\; |$$
$$\qquad NCH_2CHCH_2OCC_uH_{2u}(OCHCH_2)_wOR^{3b}$$
$$\quad\;/ \qquad\qquad\quad |$$
$$R^{2b}\qquad\quad OC_tH_{2t}(OCHCH_2)_vOR^{4b}$$
$$\qquad\qquad\quad ||\qquad\qquad |$$
$$\qquad\qquad\quad O\qquad\qquad R^{6b}$$

wherein $R^{1b}$ and $R^{2b}$ may be the same or different from each other and each represents an alkyl group having 1 to 4 carbon atoms which may be substituted with a hydroxyl group;

$R^{3b}$ and $R^{4b}$ may be the same or different from each other and each represents a linear or branched alkyl or alkenyl group having 4 to 36 carbon atoms which may be substituted with a hydroxyl group;

each of $R^{5b}$s and $R^{6b}$s represents a hydrogen atom or a methyl group;

t and u may be the same or different from each other and each represents a positive number of from 1 to 5; and v and w may be the same or different from each other and each represents a number of from 0 to 30, $$
\begin{array}{c}
R^{7c} \\
\phantom{R^{7c}} \diagdown \\
R^{8c} - N^+ CH_2CHCH_2OCC_jH_{2j}(OCHCH_2)_rOR^{10c} \quad .X^- \\
\phantom{R^{8c}} \diagup \quad\quad\quad | \\
R^{9c} \quad\quad\quad OCC_kH_{2k}(OCHCH_2)_sOR^{11c} \\
\phantom{R^{9c}\quad\quad\quad O}\| \quad\quad | \\
\phantom{R^{9c}\quad\quad\quad} O \quad R^{13c}
\end{array}
\quad (C)
$$

wherein $R^{7c}$ and $R^{8c}$ may be the same or different from each other and each represents an alkyl group having 1 to 4 carbon atoms;

$R^{9c}$ represents a hydrogen atom, a benzyl group or an alkyl group having 1 to 4 carbon atoms;

$R^{10c}$ and $R^{11c}$ may be the same or different from each other and each represents a linear or branched alkyl or alkenyl group having 4 to 36 carbon atoms which may be substituted with a hydroxyl group;

each of $R^{12c}$s and $R^{13c}$s represents a hydrogen atom or a methyl group;

j and k may be the same or different from each other and each represents a positive number of from 1 to 5;

r and s may be the same or different from each other and each represents a number of from 0 to 30; and $X^-$ represents a counter ion, $$
\begin{array}{c}
\phantom{R^{1d}-N} R^{2d} \\
\phantom{R^{1d}-N} \diagup \\
R^{1d} - N \\
\phantom{R^{1d}-N} \diagdown \\
\phantom{R^{1d}-N} R^{3d}
\end{array}
\quad (D)
$$

wherein $R^{1d}$ represents an alkyl group having 1 to 4 carbon atoms which may be substituted with a hydroxyl group;

$R^{2d}$ represents a linear or branched alkyl or alkenyl group having 1 to 36 carbon atoms which may be substituted with a hydroxyl group, a group represented by the formula: $-C_aH_{2a}-(G^1)-R^{4d}$, wherein $R^{4d}$ represents a linear or branched alkyl or alkenyl group having 5 to 36 carbon atoms which may be substituted with a hydroxyl group, $G^1$ represents a group represented by the formula: $-OCO-$ or a group represented by the formula: $-NHCO-$, and a represents a positive number of 2 to 6, a group represented by the formula:

$$
\begin{array}{c}
\phantom{-C_bH_{2b}-}O \quad R^{6d} \\
\phantom{-C_bH_{2b}-}\| \quad | \\
-C_bH_{2b}-C-(OCHCH_2)_cOR^{5d},
\end{array}
$$

wherein $R^{5d}$ represents a linear or branched alkyl or alkenyl group having 6 to 36 carbon atoms which may be substituted with a hydroxyl group, each of $R^{6d}$s represents a hydrogen atom or a methyl group, b represents a positive number of 1 to 5, and c represents a number of 0 to 30, or a group represented by the formula:

$$
\begin{array}{c}
\phantom{-C_eH_{2e}-(G^2)-C_fH_{2f}-} R^{8d} \\
\phantom{-C_eH_{2e}-(G^2)-C_fH_{2f}-} | \\
-C_eH_{2e}-(G^2)-C_fH_{2f}-(OCHCH_2)_gOR^{7d},
\end{array}
$$

wherein $R^{7d}$ represents a linear or branched alkyl or alkenyl group having 4 to 36 carbon atoms which may be substituted with a hydroxyl group, each of $R^{8d}$s represents a hydrogen atom or a methyl group, $G^2$ represents a group represented by the formula: $-OCO-$ or a group represented by the formula: $-NHCO-$, e represents a positive number of 2 to 6, f represents a positive number of 1 to 5 and a represents a number of 0 to 30; and $R^{3d}$ represents a group represented by the formula:

$$
\begin{array}{c}
\phantom{-C_hH_{2h}-(G^3)-C_iH_{2i}-} R^{10d} \\
\phantom{-C_hH_{2h}-(G^3)-C_iH_{2i}-} | \\
-C_hH_{2h}-(G^3)-C_iH_{2i}-(OCHCH_2)_xOR^{9d},
\end{array}
$$

wherein $R^{9d}$ represents a linear or branched alkyl or alkenyl group having 4 to 36 carbon atoms which may be substituted with a hydroxyl group, each of $R^{10d}$s represents a hydrogen atom or a methyl group, $G^3$ represents a group represented by the formula: $-OCO-$ or a group represented by the formula: $-NHCO-$, h represents a positive number of 2 to 6, i represents a positive number of 1 to 5, and x represents a number of 0 to 30, or a group represented by the formula:

$$
\begin{array}{c}
\phantom{-C_yH_{2y}-}O \quad R^{12d} \\
\phantom{-C_yH_{2y}-}\| \quad | \\
-C_yH_{2y}-C-(OCHCH_2)_zOR^{11d},
\end{array}
$$

wherein $R^{11d}$ represents a linear or branched alkyl or alkenyl group having 6 to 36 carbon atoms which may be substituted with a hydroxyl group, each of $R^{12d}$s represents a hydrogen atom or a methyl group, y represents a positive number of 1 to 5, and z represents a number of 0 to 30, $$
\begin{array}{c}
R^e \quad\quad R^{2e} \\
\diagdown \;+\; \diagup \\
N \quad\quad .X^- \\
\diagup \quad\quad \diagdown \\
R^{1e} \quad\quad R^{3e}
\end{array}
\quad (E)
$$

wherein $R^e$ represents a hydrogen atom, a benzyl group or an alkyl group having 1 to 4 carbon atoms which may be substituted with a hydroxyl group;

$R^{1e}$ represents an alkyl group having 1 to 4 carbon atoms which may be substituted with a hydroxyl group;

$R^{2e}$ represents a linear or branched alkyl or alkenyl group having 5 to 36 carbon atoms which may be substituted with a hydroxyl group, a group represented by the formula: $-C_aH_{2a}-(G^1)-R^{4e}$, wherein $R^{4e}$ represents a linear or branched alkyl or alkenyl group having 5 to 36 carbon atoms which may be substituted with a hydroxyl group, $G^1$ represents a group represented by the formula: $-OCO-$ or a group represented by the formula: $-NHCO-$, and a represents a positive number of 2 to 6, a group represented by the formula:

$$
\begin{array}{c}
\phantom{-C_bH_{2b}-}O \quad R^{6e} \\
\phantom{-C_bH_{2b}-}\| \quad | \\
-C_bH_{2b}-C-(OCHCH_2)_cOR^{5e},
\end{array}
$$

wherein $R^{5e}$ represents a linear or branched alkyl or alkenyl group having 6 to 36 carbon atoms which may be substituted with a hydroxyl group, each of $R^{6e}$s represents a hydrogen atom or a methyl group, b represents a positive number of 1 to 5, and c represents a number of 0 to 30, or a group represented by the formula:

$$
\begin{array}{c}
\phantom{-C_eH_{2e}-(G^2)-C_fH_{2f}-} R^{8e} \\
\phantom{-C_eH_{2e}-(G^2)-C_fH_{2f}-} | \\
-C_eH_{2e}-(G^2)-C_fH_{2f}-(OCHCH_2)_gOR^{7e},
\end{array}
$$

wherein $R^{7e}$ represents a linear or branched alkyl or alkenyl group having 4 to 36 carbon atoms which may be substituted with a hydroxyl group, each of $R^{8e}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of 0 to 30;

$R^{3e}$ represents a group represented by the formula:

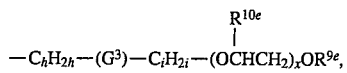

wherein $R^{9e}$ represents a linear or branched alkyl or alkenyl group having 4 to 36 carbon atoms which may be substituted with a hydroxyl group, each of $R^{10e}$s represents a hydrogen atom or a methyl group, $G^3$ represents a group represented by the formula: —OCO— or a group represented by the formula: —NHCO—, h represents a positive number of 2 to 6, i represents a positive number of 1 to 5, and x represents a number of 0 to 30, or a group represented by the formula:

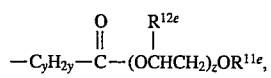

wherein $R^{11e}$ represents a linear or branched alkyl or alkenyl group having 6 to 36 carbon atoms which may be substituted with a hydroxyl group, each of $R^{12e}$s represents a hydrogen atom or a methyl group, y represents a positive number of 1 to 5, and z represents a number of 0 to 30; and $X^-$ represents a counter ion, and

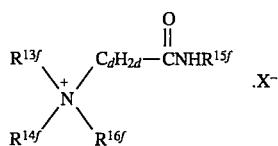

wherein $R^{13f}$ represents a hydrogen atom, a benzyl group or an alkyl group having 1 to 4 carbon atoms which may be substituted with a hydroxyl group;

$R^{14f}$ represents an alkyl group having 1 to 4 carbon atoms which may be substituted with a hydroxyl group;

$R^{15f}$ represents a linear or branched alkyl or alkenyl group having 6 to 36 carbon atoms which may be substituted with a hydroxyl group;

$R^{16f}$ represents a linear or branched alkyl or alkenyl group having 5 to 36 carbon atoms which may be substituted with a hydroxyl group; d is a positive number of 1 to 5; and $X^-$ is a counter ion.

30. The method as claimed in claim 29, wherein the enhancer and the agricultural chemical are diluted with water or a liquid carrier before applying.

31. The method as claimed in claim 29, wherein an appropriate amount of a surfactant other than the compounds represented by the above formulae (A) to (F) is further added to the composition comprising the agricultural chemical.

32. The method as claimed in claim 31, wherein the surfactant is a nonionic surfactant.

33. The method as claimed in claim 31, wherein the weight ratio of the compound(s) represented by the above formulae (A) to (F) to the surfactant(s) other than the compounds represented by the formulae (A) to (F) is from 1/10 to 50/1.

34. The method as claimed in claim 29, wherein the weight ratio of the compound(s) represented by the above formulae (A) to (F) to the agricultural chemical(s) is from 0.05 to 50.

35. The method as claimed in claim 29, wherein the weight ratio of the compound(s) represented by the above formulae (A) to (F) to the agricultural chemical is from 0.1 to 10.

36. The method as claimed in claim 29, wherein the agricultural chemical is a fungicide, an insecticide, a miticide, a herbicide or a plant growth regulator.

37. A method for enhancing the effectiveness of an agricultural chemical which comprises applying an enhancer compound of the following formula (E), with an agricultural chemical to a locus which would benefit from such treatment:

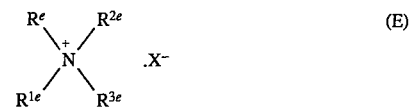

wherein $R^e$ represents a hydrogen atom, a benzyl group or an alkyl group having 1 to 4 carbon atoms which may be substituted with a hydroxyl group;

$R^{1e}$ represents an alkyl group having 1 to 4 carbon atoms which may be substituted with a hydroxyl group;

$R^{2e}$ represents a linear or branched alkyl or alkenyl group having 5 to 36 carbon atoms which may be substituted with a hydroxyl group, a group represented by the formula: —$C_aH_{2a}$—($G^1$)—$R^{4e}$, wherein $R^{4e}$ represents a linear or branched alkyl or alkenyl group having 5 to 36 carbon atoms which may be substituted with a hydroxyl group, $G^1$ represents a group represented by the formula: —OCO— or a group represented by the formula: —NHCO—, and a represents a positive number of 2 to 6, a group represented by the formula:

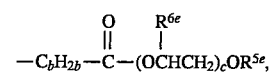

wherein $R^{5e}$ represents a linear or branched alkyl or alkenyl group having 6 to 36 carbon atoms which may be substituted with a hydroxyl group, each of $R^{6e}$s represents a hydrogen atom or a methyl group, b represents a positive number of 1 to 5, and c represents a number of 0 to 30, or a group represented by the formula:

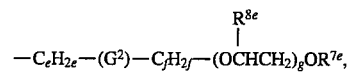

wherein $R^{7e}$ represents a linear or branched alkyl or alkenyl group having 4 to 36 carbon atoms which may be substituted with a hydroxyl group, each of $R^{8e}$s represents a hydrogen atom or a methyl group, $G^2$ represents a group represented by the formula: —OCO— or a group represented by the formula: —NHCO—, e represents a positive number of 2 to 6, f represents a positive number of 1 to 5 and g represents a number of 0 to 30;

$R^{3e}$ represents a group represented by the formula:

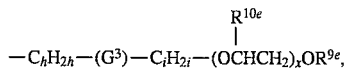

wherein $R^{9e}$ represents a linear or branched alkyl or alkenyl group having 4 to 36 carbon atoms which may be substituted with a hydroxyl group, each of $R^{10e}$s represents a hydrogen atom or a methyl group, $G^3$ represents a group represented by the formula —OCO— or a group represented by the formula: —NHCO—, h represents a positive number of 2 to 6, i represents a positive number of 1 to 5, and x represents a number of 0 to 30, or a group represented by the formula:

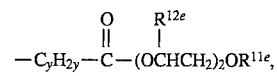

wherein $R^{11e}$ represents a linear or branched alkyl or alkenyl group having 6 to 36 carbon atoms which may be substituted with a hydroxyl group, each of $R^{12e}$s represents a hydrogen atom or a methyl group, y represents a positive number of 1 to 5, and z represents a number of 0 to 30; and $X^-$ represents a counter ion.

* * * * *